US012702672B2

(12) United States Patent
Koizumi et al.

(10) Patent No.: US 12,702,672 B2
(45) Date of Patent: Aug. 11, 2026

(54) AGENT FOR PROMOTING CORNEAL ENDOTHELIAL CELL ADHESION

(71) Applicants: Senju Pharmaceutical Co., Ltd., Osaka (JP); Shigeru Kinoshita, Osaka (JP)

(72) Inventors: Noriko Koizumi, Kyoto (JP); Shigeru Kinoshita, Osaka (JP); Morio Ueno, Kyoto (JP)

(73) Assignees: Senju Pharmaceutical Co., Ltd., Osaka (JP); Shigeru Kinoshita, Osaka (JP)

( * ) Notice: Subject to any disclaimer, the term of this patent is extended or adjusted under 35 U.S.C. 154(b) by 0 days.

(21) Appl. No.: 18/182,873

(22) Filed: Mar. 13, 2023

(65) Prior Publication Data

US 2023/0210864 A1 Jul. 6, 2023

Related U.S. Application Data

(63) Continuation of application No. 14/879,658, filed on Oct. 9, 2015, now Pat. No. 11,633,404, which is a continuation of application No. 12/675,475, filed as application No. PCT/JP2008/065459 on Aug. 28, 2008, now Pat. No. 9,248,125.

(30) Foreign Application Priority Data

Aug. 29, 2007 (JP) ................................ 2007-223141
Jan. 28, 2008 (JP) ................................ 2008-016088

(51) Int. Cl.

| | |
|---|---|
| ***A61K 31/551*** | (2006.01) |
| ***A61K 9/00*** | (2006.01) |
| ***A61K 31/4409*** | (2006.01) |
| ***A61K 31/496*** | (2006.01) |
| ***C07D 213/81*** | (2006.01) |
| ***C07D 401/12*** | (2006.01) |
| ***C12N 5/079*** | (2010.01) |

(52) U.S. Cl.

CPC .......... *A61K 31/551* (2013.01); *A61K 9/0048* (2013.01); *A61K 31/4409* (2013.01); *A61K 31/496* (2013.01); *C07D 213/81* (2013.01); *C07D 401/12* (2013.01); *C12N 5/0621* (2013.01); *C12N 2501/70* (2013.01)

(58) Field of Classification Search

None

See application file for complete search history.

(56) References Cited

U.S. PATENT DOCUMENTS 4,678,783 A 7/1987 Hidaka et al.
5,906,819 A 5/1999 Kaibuchi et al.
6,218,410 B1 4/2001 Uehata et al.
6,329,547 B1 12/2001 Shirasawa et al.
6,673,812 B1 1/2004 Azuma et al.
7,109,208 B2 9/2006 Takayama et al.
7,141,428 B2 11/2006 McKerracher
7,867,999 B1 1/2011 Chen et al.
9,248,125 B2 * 2/2016 Koizumi ............ A61K 31/4409
11,633,404 B2 * 4/2023 Koizumi ................ A61P 43/00
514/253.05
11,839,618 B2 * 12/2023 Koizumi ............. A61K 31/496
2004/0106646 A1 6/2004 Takayama et al.
2004/0138286 A1 7/2004 Imazaki et al.
2004/0213782 A1 10/2004 Wax
2005/0096310 A1 5/2005 Yamada et al.
2005/0214259 A1 9/2005 Sano et al.
2006/0122214 A1 6/2006 Kai et al.
2006/0252765 A1 11/2006 Takayama et al.
2007/0093513 A1 4/2007 Takayama et al.
2007/0129404 A1 6/2007 Hagihara et al.
2007/0179127 A1 8/2007 Yamada et al.
2007/0238173 A1 10/2007 Yamagami et al.
2010/0209402 A1 8/2010 Koizumi et al.
2016/0030410 A1 2/2016 Koizumi et al.
2016/0101113 A1 4/2016 Koizumi et al.

FOREIGN PATENT DOCUMENTS

| | | | |
|---|---|---|---|
| AU | 199896461 | A1 | 5/1999 |
| CN | 1358102 | A | 7/2002 |
| CN | 1777445 | A | 5/2006 |
| EP | 1541559 | A1 | 6/2005 |
| EP | 1616577 | A1 | 1/2006 |
| EP | 1829876 | A1 | 9/2007 |
| EP | 1980274 | A1 | 10/2008 |
| EP | 2193806 | A1 | 6/2010 |
| JP | 10-113187 | A | 5/1998 |
| JP | 3421217 | B2 | 6/2003 |
| JP | 2004-024852 | A | 1/2004 |

(Continued)

OTHER PUBLICATIONS

U.S. Appl. No. 14/879,658, filed Oct. 9, 2015.
U.S. Appl. No. 12/675,475, filed May 5, 2010.
U.S. Appl. No. 14/879,857, filed Oct. 9, 2015.
Anderson et al., "Rho and Rho-kinase (ROCK) signaling in adherens and gap junction assembly in corneal epithelium," *Investigative Ophthalmology & Visual Science*, 43(4): 978-986 (2002).
Bourne, "Functional Measurements on the Enlarged Endothelial Cells of Corneal Transplants," *Trans. Am. Ophthalmol. Soc.*, 93: 65-82 (1993).
Colby, "Medical Treatment of Fuchs' Dystrophy in our Lifetime?" *Investigative Ophthalmology & Visual Science*, 54(4): 2503 (Apr. 2013).

(Continued)

*Primary Examiner* — Blaine Lankford
(74) *Attorney, Agent, or Firm* — Leydig, Voit & Mayer, Ltd.

(57) ABSTRACT

The invention provides an agent for promoting adhesion of a corneal endothelial cell, containing a Rho kinase inhibitor, as well as a culture medium for a corneal endothelial cell, a solution for preservation of cornea, and a method of producing a corneal endothelial preparation, which includes culturing the corneal endothelial cell using the aforementioned culture medium.

16 Claims, 12 Drawing Sheets

(56) References Cited

FOREIGN PATENT DOCUMENTS

| | | | |
|---|---|---|---|
| JP | 2005-229869 | A | 9/2005 |
| JP | 5657252 | B2 | 1/2015 |
| KR | 10-2005-0111645 | A | 11/2005 |
| RU | 2249591 | C2 | 9/2001 |
| WO | WO 1998/052937 | A2 | 11/1998 |
| WO | WO 1999/020620 | A1 | 4/1999 |
| WO | WO 1999/061403 | A1 | 12/1999 |
| WO | WO 2001/074393 | A1 | 10/2001 |
| WO | WO 2002/076976 | A2 | 10/2002 |
| WO | WO 2002/076977 | A2 | 10/2002 |
| WO | WO 2002/100833 | A1 | 12/2002 |
| WO | WO 2003/059913 | A1 | 7/2003 |
| WO | WO 2003/062227 | A1 | 7/2003 |
| WO | WO 2003/092762 | A1 | 11/2003 |
| WO | WO 2004/009555 | A1 | 1/2004 |
| WO | WO 2004/022541 | A1 | 3/2004 |
| WO | WO 2004/108724 | A1 | 12/2004 |
| WO | WO 2005/003101 | A2 | 1/2005 |
| WO | WO 2005/034866 | A2 | 4/2005 |
| WO | WO 2005/035501 | A1 | 4/2005 |
| WO | WO 2005/035503 | A1 | 4/2005 |
| WO | WO 2005/035506 | A1 | 4/2005 |
| WO | WO 2005/037197 | A2 | 4/2005 |
| WO | WO 2005/037198 | A2 | 4/2005 |
| WO | WO 2005/039564 | A1 | 5/2005 |
| WO | WO 2005/078071 | A1 | 8/2005 |
| WO | WO 2005/080394 | A1 | 9/2005 |
| WO | WO 2005/103050 | A2 | 11/2005 |
| WO | WO 2005/118582 | A1 | 12/2005 |
| WO | WO 2006/057270 | A1 | 6/2006 |
| WO | WO 2007/018226 | A1 | 2/2007 |
| WO | WO 2007/026664 | A1 | 3/2007 |
| WO | WO 2007/043255 | A1 | 4/2007 |
| WO | WO 2007/083685 | A1 | 7/2007 |
| WO | WO 2002/083175 | A1 | 10/2010 |

OTHER PUBLICATIONS

Gagnon et al., "Corneal Endothelial Cell Density in Glaucoma," *Cornea*, 16(3): 314-318 (1997).

Giaconi, "Glaucomas: Glaucoma and the Cornea," (chapter 47) in *Pearls of Glaucoma Management* (J.A. Giaconi et al., eds.), pp. 363-369 (2010).

Goodman, "Eyedrops Using Novel Compound Restore Corneal Cells," Medscape Medical News, Article 814596 (Nov. 18, 2013).

Gorovoy et al., "Recognizing and Treating Corneal Endothelial Disease," *Ophthalmology Management*, Special Cornea Issue, Article 104382 (Jun. 1, 2010).

Guo et al., "Benzalkonium chloride induces dephosphorylation of Myosin light chain in cultured corneal epithelial cells," *Investigative Ophthalmology & Visual Science*, 48(5): 2001-2008 (May 2007).

Guthoff et al., "Epithelial Innervation of Human Cornea: A Three-Dimensional Study Using Confocal Laser Scanning Fluorescence Microscopy," *Cornea*, 24(5): 608-613 (2005).

Honjo et al., "Effects of protein kinase inhibitor, HA1077, on intraocular pressure and outflow facility in rabbit eyes," *Arch Ophthalmol.*, 119(8): 1171-1178 (2001).

Huang et al., "Active iris mechanics and pupillary block: steady-state analysis and comparison with anatomical risk factors," *Annals of Biomedical Engineering*, 32(9): 1276-1285 (2004).

Huttenlocher et al., "Adhesion in cell migration," *Current Opinion in Cell Biology*, 7(5): 697-706 (Jan. 1995).

Ishizaki et al., "Pharmacological Properties of Y-27632, a Specific Inhibitor of Rho-Associated Kinases," *Mol. Pharmacol.*, 57(5): 976-983 (2000).

Ivanišević et al., "The incidence and seasonal variations of acute primary angle-closure glaucoma," *Coll. Antropol.*, 26(1): 41-45 (2002).

Jacobs et al., "The Structure of Dimeric ROCK I Reveals the Mechanism for Ligand Selectivity," *J. Biol. Chem.*, 281(1): 260-268 (2006).

Kaufman, "The corneal endothelium in intraocular surgery," *Journal of the Royal Society of Medicine*, 73(3): 165-171 (Mar. 1980).

Knorz et al., "Laser in Situ Keratomileusis for Moderate and High Myopia and Myopic Astigmatism," *Ophthalmology*, 105(5): 932-940 (1998).

Koizumi, "II. Regenerative Engineering of Visual Function: Regenerative Engineering of Anterior Segment of the eye (6) Development of Cultivated Corneal Endothelial Sheet Transplantation using Monkeys," *Japanese Journal of Clinical Ophthalmology*, 59(11): 197-201 (2005).

Lee et al., "FGF-2 induced reorganization and disruption of actin cytoskeleton through PI 3-kinase, Rho, and Cdc42 in corneal endothelial cells," *Molecular Vision*, 9: 624-634 (2003).

Lee et al., "FGF-2-induced wound healing in corneal endothelial cells requires Cdc42 activation and Rho inactivation through the phosphatidylinositol 3-kinase pathway," *Investigative Ophthalmology & Visual Science*, 47(4): 1376-1386 (2006).

Nakamura et al., "Role of the small GTP-binding protein rho in epithelial cell migration in the rabbit cornea," *Investigative Ophthalmology & Visual Science*, 42(5): 941-947 (Apr. 2001).

Narumiya et al., "Use and properties of ROCK-specific inhibitor Y-27632," *Methods Enzymol.*, 325: 273-284 (2000).

Nishimaru et al., "Inhibition of Agonist-Induced Positive Inotropy by a Selective Rho-Associated Kinase Inhibitor, Y-27632," *J. Pharmacol. Sci.*, 92(4): 424-427 (2003).

Okumura et al., "Enhancement on primate corneal endothelial cell survival in vitro by a ROCK inhibitor," *Investigative Ophthalmology & Visual Science*, 50(8): 3680-3687 (Aug. 2009).

Okumura et al., "ROCK Inhibitor Converts Corneal Endothelial Cells into a Phenotype Capable of Regenerating In Vivo Endothelial Tissue," *Am. J. Pathol.*, 181(1): 268-277 (2012).

Okumura et al., "The ROCK inhibitor eye drop accelerates corneal endothelium wound healing," *Investigative Ophthalmology & Visual Science*, 54(4): 2439-2502 (Apr. 2013).

Okumura et al., "Involvement of Cyclin D and p27 in Cell Proliferation Mediated by ROCK Inhibitors Y-27632 and Y-39983 During Corneal Endothelium Wound Healing," *Invest. Ophthalmol. Vis. Sci.*, 55(1): 318-329 (2014).

Okumura et al., "Effect of the Rho Kinase Inhibitor Y-27632 on Corneal Endothelial Wound Healing," *Investigative Ophthalmology & Visual Science*, 56(10): 6067-6074 (2015).

Okumura et al., "Effect of the Rho-Associated Kinase Inhibitor Eye Drop (Ripasudil) on Corneal Endothelial Wound Healing," *Invest. Ophthalmol. Vis. Sci.*, 57(3): 1284-1292 (2016).

Quigley et al., "Possible mechanisms of primary angle-closure and malignant glaucoma," *Journal of Glaucoma*, 12(2): 167-180 (2003).

Riento et al., "Rocks: multifunctional kinases in cell behavior," *Nature Reviews Molecular Cell Biology*, 4(6): 446-456 (Jun. 2003).

Sawada et al., "Inhibition of Rho-Associated Kinase Results in Suppression of Neointimal Formation of Balloon-Injured Arteries," Circulation, 101(17): 2030-2033 (2000).

Satpathy et al., "Thrombin-induced phosphorylation of the regulatory light chain of myosin II in cultured bovine corneal endothelial cells," *Experimental Eye Research*, 79(4): 477-486 (2004).

Shibuya et al., "Effect of Fasudil HCl, a Protein Kinase Inhibitor, on Cerebral Vasospasm," *Acta Neurochir. Suppl.*, 77: 201-204 (2001).

Spadea et al., "Specular microscopy of the corneal endothelium after excimer laser photorefractive keratectomy," *J. Cataract Refract. Surg.*, 22(2): 188-193 (1996).

Svoboda et al., "ROCK inhibitor (Y27632) increases apoptosis and disrupts the actin cortical mat in embryonic avian corneal epithelium," *Developmental Dynamics*, 229: 579-590 (Jan. 2004).

Tavakoli et al., "Corneal Sensitivity Is Reduced and Relates to the Severity of Neuropathy in Patient With Diabetes," *Diabetes Care.*, 30(7): 1895-1897 (2007).

Terry et al., "Deep lamellar endothelial keratoplasty (DLEK): pursuing the ideal goals of endothelial replacement," *Eye*, 17(8): 982-988 (2003).

Tian et al., "Effects of the Rho kinase inhibitor Y-27632 and the phosphatase inhibitor calyculin A on outflow facility in monkeys," *Experimental Eye Research*, 80: 215-225 (2005).

Thakur et al., "Endothelial cell loss after small incision cataract surgery," *Nepal J. Ophthalmol.*, 3(2): 177-180 (2011).

(56) References Cited

OTHER PUBLICATIONS

Tsuru et al., "Endothelial wound-healing of monkey cornea: fluorophotometric and specular microscopic studies," *Jpn. J. Ophthalmol.*, 28(2): 105-125 (1984).
U.S. National Library of Medicine (National Institutes of Health), "Fuchs' dystrophy," *Medline Plus*, Article 007295 (Sep. 2, 2014).
Ventura et al., "Corneal thickness and endothelial density before and after cataract surgery," *Br. J. Ophthalmol.*, 85(1): 18-20 (2001).
Watanabe et al., "A ROCK inhibitor permits survival of dissociated human embryonic stem cells," *Nature Biotechnology*, 25: 681-686 (2007).
Yin et al., "Rho kinases regulate corneal epithelial wound healing," *Am. J. Physiol. Cell Physiol.*, 295(2): C378-C387 (2008).
Brazilian Patent Office, Unfavorable Opinion in Brazilian Patent Application No. PI0816182-8 (Jul. 17, 2018).
Brazilian Patent Office, Non-Final Rejection Decision in Brazilian Patent Application No. PI0816182-8 (Mar. 21, 2019).
Canadian Patent Office, Examination Search Report in Canadian Patent Application No. 2,697,895 (Sep. 1, 2015).
Canadian Patent Office, Office Action in Canadian Patent Application No. 2,697,895 (Oct. 20, 2016).
China National Intellectual Property Administration, Office Action in Chinese Patent Application No. 201410200380.3 (Feb. 16, 2015).
China National Intellectual Property Administration, First Office Action in Chinese Patent Application No. 201410200362.5 (Jul. 3, 2015).
European Patent Office, Extended European Search Report in European Patent Application No. 08828145.6 (Feb. 23, 2011).
European Patent Office, Communication Pursuant to Article 94(3) EPC in European Patent Application No. 08 828 145.6 (Jan. 15, 2016).
Intellectual Property India, First Examination Report in Indian Patent Application No. 1686/CHENP/2010 (Aug. 28, 2015).
Intellectual Property India, Hearing Notice in Indian Patent Application No. 1686/CHENP/2010 (Dec. 28, 2017).
Japan Patent Office, International Search Report in International Patent Application No. PCT/JP2008/065459 (Oct. 7, 2008).
Japan Patent Office, International Written Opinion in International Patent Application No. PCT/JP2008/065459 (Oct. 7, 2008).
Japan Patent Office, Office Action in Japanese Patent Application No. 2009-530186 (Oct. 3, 2014).
Japan Patent Office, Japanese Office Action in Japanese Patent Application No. 2013-105593 (Jan. 28, 2015).
Japan Patent Office, Office Action in Japanese Patent Application No. 2014-216143 (Aug. 24, 2015).
Japan Patent Office, Office Action in Japanese Patent Application No. 2021-025578 (Jan. 19, 2022).
Japan Patent Office, Final Official Action in Japanese Patent Application No. 2021-025578 (Jun. 17, 2022).
Korean Intellectual Property Office, Office Action in Korean Patent Application No. 9-5-2015-019153641 (Mar. 23, 2015).
Korean Intellectual Property Office, Notice of Final Rejection in Korean Patent Application No. 10-2010-7006685 (Apr. 17, 2015).
Korean Intellectual Property Office, Office Action in Korean Patent Application No. 10-2015-7018932 (Oct. 16, 2015).
Korean Intellectual Property Office, Notice of Final Rejection in Korean Patent Application No. 10-2014-7033392 (Nov. 23, 2015).
Korean Intellectual Property Office, Decision on the Appeal of the Final Rejection in Korean Patent Application No. 10-2010-7006685 (Mar. 17, 2017).
Korean Intellectual Property Office, Decision on the Appeal of the Final Rejection in Korean Patent Application No. 10-2014-7033392 (Mar. 17, 2017).
Korean Intellectual Property Office, Notice of Final Rejection in Korean Patent Application No. 10-2015-7018932 (Nov. 21, 2017).
Korean Intellectual Property Office, Notice of Preliminary Rejection in Korean Patent Application No. 10-2018-7007476 (May 16, 2018).
Korean Intellectual Property Office, Notice of Final Rejection in Korean Patent Application No. 10-2018-7007476 (Mar. 28, 2019).
Korean Intellectual Property Office, Decision Issued by the Intellectual Property Trial and Appeal Board in Appeal No. 7-7-2019-008555009 for Korean Patent Application 2015-7018932 (Oct. 29, 2019).
Korean Intellectual Property Office, Notice of Preliminary Rejection in Korean Patent Application No. 10-2019-7022179 (Nov. 6, 2019).
Korean Intellectual Property Office, Notice of Final Rejection in Korean Patent Application No. 10-2019-7022179 (Mar. 9, 2021).
Korean Intellectual Property Office, Notice of the Result of Reexamination in Korean Patent Application No. 10-2019-7022179 (Aug. 9, 2021).
Korean Intellectual Property Office, Notice of Preliminary Rejection in Korean Patent Application No. 10-2021-7017484 (Sep. 13, 2021).
Korean Intellectual Property Office, Notice of Final Rejection in Korean Patent Application No. 10-2021-7017484 (May 27, 2022).
Korean Intellectual Property Office, Intellectual Property Trial and Appeal Board Decision in Korean Patent Application No. 10-2019-7022179 (Sep. 28, 2022).
Korean Intellectual Property Office, Result of Reexamination in Korean Patent Application No. 10-2021-7017484 (Dec. 27, 2022).
Brazil National Institute of Industrial Property, Written Opinion in Brazilian Patent Application No. PI0816182-8 (Jun. 1, 2023).
Korean Intellectual Property Office, Office Action in Korean Patent Application No. 10-2024-7009980 (Sep. 29, 2024).
Korean Intellectual Property Office, Office Action in Korean Patent Application No. 10-2024-7009980 (Feb. 25, 2026).

* cited by examiner

A

B

*: p<0.001, Student's t-test

*: p<0.001, Student's t-test

A

B

A

B

A

B

C

| | Control | Y-27632 |
|---|---|---|
| cell area (-fold) | ~1.0 | ~1.6 |

*P<0.01, Student's t-test, n=5

A

B

A

B

A

B

C

D

*P<0.01, Student's t-test

AGENT FOR PROMOTING CORNEAL ENDOTHELIAL CELL ADHESION

CROSS-REFERENCE TO RELATED APPLICATIONS

This patent application is a continuation of U.S. patent application Ser. No. 14/879,658, filed Oct. 9, 2015, which is a continuation of U.S. patent application Ser. No. 12/675,475, filed May 5, 2010, now U.S. Pat. No. 9,248,125, which is the U.S. national phase of International Patent Application PCT/JP2008/065459, filed Aug. 28, 2008, which claims the benefit of Japanese Patent Application No. 2008-016088, filed Jan. 28, 2008, and Japanese Patent Application No. 2007-223141, filed Aug. 29, 2007, which are incorporated by reference in their entireties herein.

TECHNICAL FIELD

The present invention relates to an agent for promoting corneal endothelial cell adhesion, which is used for adhesion, maintenance or preservation of corneal endothelial cells.

BACKGROUND ART

Visual information is recognized when the light that entered from the cornea (transparent tissue at the forefront of the eyeball) reaches the retina to excite retinal nerve cells, and the developed electric signals are transmitted to the cerebral visual cortex via the optic nerve. To have good eyesight, the cornea needs to be transparent. The transparency of the cornea is maintained when the water content is kept at a constant level by the pumping function and barrier function of the corneal endothelial cells.

The density of the corneal endothelial cells of human is about 3000 cells per 1 $mm^2$ at birth. Once damaged, the cells lose an ability to regenerate. In endothelial corneal dystrophy and bullous keratopathy resulting from functional disorder of corneal endothelium due to various causes, the cornea suffers from edema and opacity, and the eyesight decreases markedly. At present, bullous keratopathy is treated by penetrating keratoplasty wherein the entire three-layer structure of epithelium, parenchyma and endothelium of the cornea is transplanted. However, donation of cornea is insufficient in Japan and, although there are about 5500 waiting patients of corneal transplantation, about 2700 corneal transplants are performed annually in Japan.

In recent years, the idea of "parts transplantation" for transplanting only the damaged tissue has been attracting attention for the purpose of decreasing the risk of rejection reaction and postoperative complications, thereby affording better visual function. Of the corneal transplants, epithelial transplantation for transplanting only the corneal epithelium, cultured oral mucosa epithelial transplantation for transplanting oral mucosa instead of corneal epithelium, Lamina profunda lamellar keratoplasty for transplanting parenchymal tissue and the like have been performed. A method of transplanting only the corneal endothelium is also considered. For transplantation of corneal endothelium, a corneal endothelium-like sheet consisting of a corneal endothelium layer cultured on a collagen layer is known (see patent documents 1 and 2). However, as for corneal endothelial cells, particularly those derived from human, since the number of corneal donors is limited and in vitro culture is difficult, production of cultured cells in the number necessary for transplantation requires time and cost.

Human embryonic stem (ES) cell shows high autoreplicatability and multipotency, and is drawing attention from the aspect of medicine application. However, it has a practical problem of drastically reduced cell number, since an operation to disperse the cells in a culture step easily causes cell death. Recently, it has been found that the cell death that occurs during culture of human ES cells is caused by the activation of Rho kinase (ROCK), and inhibition of ROCK markedly suppresses cell death, and reported that, using a ROCK inhibitor such as Y-27632 and the like, mass culture of human ES cell and production of cerebral cells can be enabled (non-patent document 1).

Rho kinase (ROCK) inhibitors are known to have various actions. For example, patent document 3 discloses that Rho kinase inhibitors promote corneal neurite formation, and that Rho kinase inhibitors are used as an agent for recovering corneal perception. In addition, patent document 4 discloses that Rho kinase inhibitors have an axon outgrowth promoting action on retinal ganglion cells, and are used for the treatment of vision dysfunction.

patent document 1: JP-A-2004-24852
patent document 2: JP-A-2005-229869
patent document 3: WO2005/118582
patent document 4: WO2002/083175
non-patent document 1: Nat Biotechnol. 2007, 25, 681

DISCLOSURE OF THE INVENTION

Problems to be Solved by the Invention

An object of the present invention is to provide a means capable of efficiently adhering a corneal endothelial cell and a means to stably supply a corneal endothelial preparation.

Means of Solving the Problems

The present inventors have conducted intensive studies in view of the aforementioned problems and found that adhesion of corneal endothelial cells to a culture substrate can be strikingly promoted by culturing the cell in the presence of a Rho kinase inhibitor, which resulted in the completion of the present invention. Accordingly, the present invention provides the following.

[1] An agent for promoting adhesion of a corneal endothelial cell, comprising a Rho kinase inhibitor.

[2] The agent of the aforementioned [1], wherein the Rho kinase inhibitor is at least one selected from the group consisting of (+)-trans-4-(1-aminoethyl)-1-(4-pyridylcarbamoyl)cyclohexane, 1-(5-isoquinolinesulfonyl)homopiperazine and a pharmacologically acceptable salt thereof.

[3] The agent of the aforementioned [1], wherein the corneal endothelial cell is derived from human.

[4] The agent of any of the aforementioned [1] to [3], which is a preparation for the prophylaxis or treatment of a corneal endothelial dysfunction.

[5] The agent of the aforementioned [4], which is in the form of an intracameral injection or intraocular perfusion fluid.

[6] A culture medium for a corneal endothelial cell, comprising a Rho kinase inhibitor.

[7] The culture medium of the aforementioned [6], wherein the Rho kinase inhibitor is at least one selected from the group consisting of (+)-trans-4-(1-aminoethyl)-1-(4-pyridylcarbamoyl)cyclohexane, 1-(5-isoquinolinesulfonyl)homopiperazine and a pharmacologically acceptable salt thereof.

[8] The culture medium of the aforementioned [6], wherein the corneal endothelial cell is derived from human.

[9] A corneal preservation solution comprising a Rho kinase inhibitor.

[10] The preservation solution of the aforementioned [9], wherein the Rho kinase inhibitor is at least one selected from the group consisting of (+)-trans-4-(1-aminoethyl)-1-(4-pyridylcarbamoyl)cyclohexane, 1-(5-isoquinolinesulfonyl) homopiperazine and a pharmacologically acceptable salt thereof.

[11] The preservation solution of the aforementioned [9], wherein the cornea is derived from human.

[12]A method of producing a corneal endothelial preparation, comprising a step of culturing a corneal endothelial cell using the culture medium of any of the aforementioned [6] to [8].

[13] The method of the aforementioned [12], wherein the corneal endothelial cell is derived from human.

[14] Use of a Rho kinase inhibitor for the production of an agent for promoting adhesion of a corneal endothelial cell.

[15] The use of the aforementioned [14], wherein the Rho kinase inhibitor is at least one selected from the group consisting of (+)-trans-4-(1-aminoethyl)-1-(4-pyridylcarbamoyl)cyclohexane, 1-(5-isoquinolinesulfonyl)homopiperazine and a pharmacologically acceptable salt thereof.

[16] The use of the aforementioned [14], wherein the corneal endothelial cell is derived from human.

[17] The use of any of the aforementioned [14] to [16], wherein the agent for promoting adhesion of a corneal endothelial cell is a preparation for prophylaxis or treatment of corneal endothelial dysfunction.

[18] The use of the aforementioned [17], wherein the agent for promoting adhesion of a corneal endothelial cell is in the form of an intracameral injection or intraocular perfusion fluid.

[19] Use of a Rho kinase inhibitor for the production of a culture medium for a corneal endothelial cell.

[20] The use of the aforementioned [19], wherein the Rho kinase inhibitor is at least one selected from the group consisting of (+)-trans-4-(1-aminoethyl)-1-(4-pyridylcarbamoyl)cyclohexane, 1-(5-isoquinolinesulfonyl)homopiperazine and a pharmacologically acceptable salt thereof.

[21] The use of the aforementioned [19], wherein the corneal endothelial cell is derived from human.

[22] Use of a Rho kinase inhibitor for the production of a corneal preservation solution.

[23] The use of the aforementioned [22], wherein the Rho kinase inhibitor is at least one selected from the group consisting of (+)-trans-4-(1-aminoethyl)-1-(4-pyridylcarbamoyl)cyclohexane, 1-(5-isoquinolinesulfonyl)homopiperazine and a pharmacologically acceptable salt thereof.

[24] The use of the aforementioned [22], wherein the cornea is derived from human.

[25]A method of promoting adhesion of a corneal endothelial cell, comprising contacting an effective amount of a Rho kinase inhibitor with a target or corneal endothelial cell in need of promotion of adhesion of the corneal endothelial cell.

[26] The method of the aforementioned [25], wherein the Rho kinase inhibitor is at least one selected from the group consisting of (+)-trans-4-(1-aminoethyl)-1-(4-pyridylcarbamoyl)cyclohexane, 1-(5-isoquinolinesulfonyl)homopiperazine and a pharmacologically acceptable salt thereof.

[27] The method of the aforementioned [25], wherein the corneal endothelial cell is derived from human.

[28] The method of the aforementioned [25], which aims to prevent or treat corneal endothelial dysfunction.

[29] The method of the aforementioned [25], comprising administering an effective amount of a Rho kinase inhibitor in the form of an intracameral injection or intraocular perfusion fluid.

[30]A method of culturing a corneal endothelial cell, comprising a step of culturing the corneal endothelial cell using a culture medium comprising a Rho kinase inhibitor.

[31] The method of the aforementioned [30], wherein the Rho kinase inhibitor is at least one selected from the group consisting of (+)-trans-4-(1-aminoethyl)-1-(4-pyridylcarbamoyl)cyclohexane, 1-(5-isoquinolinesulfonyl)homopiperazine and a pharmacologically acceptable salt thereof.

[32] The method of the aforementioned [30], wherein the corneal endothelial cell is derived from human.

[33]A method of protecting cornea, comprising a step of retaining a corneal graft or corneal endothelial cell in a cornea protection solution comprising a Rho kinase inhibitor.

[34] The method of the aforementioned [33], wherein the Rho kinase inhibitor is at least one selected from the group consisting of (+)-trans-4-(1-aminoethyl)-1-(4-pyridylcarbamoyl)cyclohexane, 1-(5-isoquinolinesulfonyl)homopiperazine and a pharmacologically acceptable salt thereof.

[35] The method of the aforementioned [33], wherein the cornea is derived from human.

[36]A method of producing a corneal endothelial preparation, comprising a step of culturing the corneal endothelial cell using a culture medium comprising a Rho kinase inhibitor.

[37] The method of the aforementioned [36], wherein the Rho kinase inhibitor is at least one selected from the group consisting of (+)-trans-4-(1-aminoethyl)-1-(4-pyridylcarbamoyl)cyclohexane, 1-(5-isoquinolinesulfonyl)homopiperazine and a pharmacologically acceptable salt thereof.

[38] The method of the aforementioned [36] wherein the corneal endothelial cell is derived from human.

[39]A method of treating bullous keratopathy, corneal edema or corneal leukoma, comprising a step of culturing a corneal endothelial cell using a culture medium comprising a Rho kinase inhibitor, and a step of transplanting the corneal endothelial preparation obtained in the aforementioned culture step into a subject in need of transplantation of the corneal endothelium.

[40] The method of the aforementioned [39], wherein the Rho kinase inhibitor is at least one selected from the group consisting of (+)-trans-4-(1-aminoethyl)-1-(4-pyridylcarbamoyl)cyclohexane, 1-(5-isoquinolinesulfonyl)homopiperazine and a pharmacologically acceptable salt thereof.

[41] The method of the aforementioned [39], wherein the corneal endothelial cell is derived from human.

Effect of the Invention

The agent for promoting adhesion of a corneal endothelial cell of the present invention contains a Rho kinase inhibitor as an active ingredient. The agent for promoting adhesion of a corneal endothelial cell of the present invention promotes adhesion of the corneal endothelial cell and enables formation of a corneal endothelial cell layer having good cell morphology and high cell density. Therefore, it is useful as a therapeutic agent or prophylactic agent for a disease accompanied by corneal endothelial dysfunction, such as bullous keratopathy and corneal endotheliitis. The agent for promoting adhesion of a corneal endothelial cell of the present invention is useful as an agent for protecting corneal endothelium in the treatment or prophylaxis of a disease accompanied by a corneal endothelial dysfunction. Furthermore, the agent for promoting adhesion of a corneal endothelial cell of the present invention can be utilized as an agent for protecting corneal endothelium in the treatment or prophylaxis of corneal endothelial dysfunction associated with an intraocular surgery such as cataract surgery, vitreous surgery and the like, corneal endothelial dysfunction caused by increased intraocular pressure (particularly glaucomatous attack), or corneal endothelial dysfunction caused by insufficient oxygen due to contact lenses. Since the culture medium or corneal preservation solution of the present invention contains a Rho kinase inhibitor, corneal endothelial cells can be cultured, maintained or preserved fine, and stable supply, maintenance or preservation of a corneal endothelial preparation is enabled.

BRIEF DESCRIPTION OF THE DRAWINGS

FIG. 12A shows day 1 of passage culture of the ROCK inhibitor(−) group, B shows day 2 of passage culture of the ROCK inhibitor(−) group, C shows day 1 of passage culture of the ROCK inhibitor(+) group, and D shows day 2 of passage culture of the ROCK inhibitor(+) group.

BEST MODE FOR CARRYING OUT THE INVENTION

Figure 1:
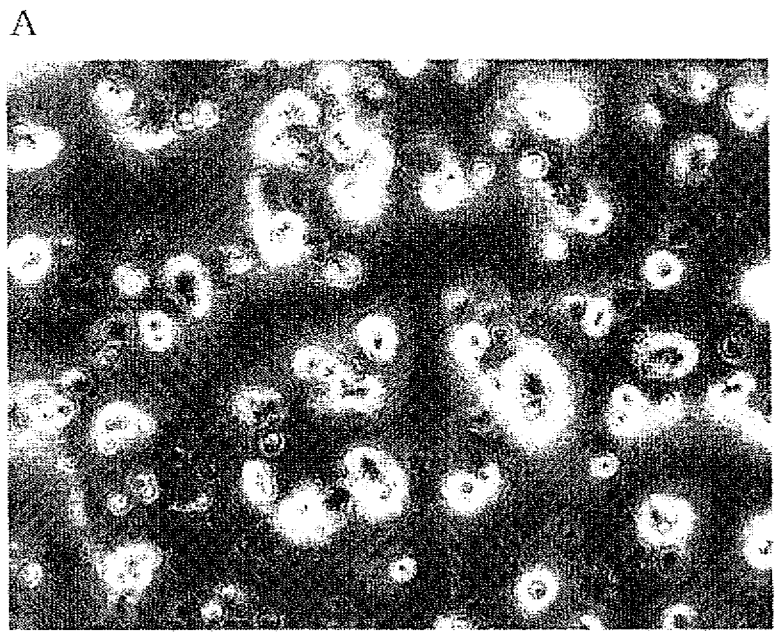
FIG. 1 is a phase contrast photomicrograph of the primary culture of rabbit corneal endothelial cells (after 24 hr from the start of the culture, magnification: 100-fold).
Figure 1:
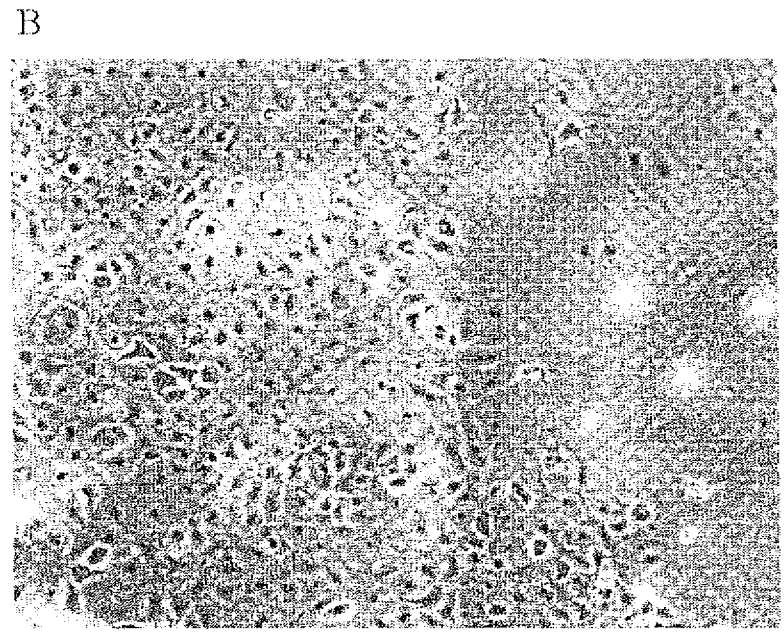

The agent for promoting adhesion of a corneal endothelial cell of the present invention (hereinafter sometimes to be abbreviated as "adhesion promoter of the present invention") contains a Rho kinase inhibitor as an active ingredient.

In the present invention, Rho kinase means serine/threonine kinase activated along with the activation of Rho. Examples include ROKα (ROCKII: Leung, T. et al., J. Biol. Chem., 270, 29051-29054, 1995), p160ROCK (ROKβ, ROCK-I: Ishizaki, T. et al., The EMBO J., 15(8), 1885-1893, 1996) and other proteins having a serine/threonine kinase activity.

In the present invention, one kind of Rho kinase inhibitor may be contained singly, or several kinds may be contained in combination as necessary.

Examples of the Rho kinase inhibitor include compounds disclosed in the following references: U.S. Pat. Nos. 4,678,783, 3,421,217, WO99/20620, WO99/61403, WO02/076976, WO02/076977, WO02/100833, WO03/059913, WO03/062227, WO2004/009555, WO2004/022541, WO2004/108724, WO2005/003101, WO2005/039564, WO2005/034866, WO2005/037197, WO2005/037198, WO2005/035501, WO2005/035503, WO2005/035506, WO2005/080394, WO2005/103050, WO2006/057270, WO2007/026664 and the like. Such compounds can be produced according to the method described in each of the disclosed references. Specific examples include 1-(5-isoquinolinesulfonyl)homopiperazine (fasudil), (+)-trans-4-(1-aminoethyl)-1-(4-pyridylcarbamoyl)cyclohexane (Y-27632) and the like. As these compounds, commercially available products can be preferably used.

Of these, (+)-trans-4-(1-aminoethyl)-1-(4-pyridylcarbamoyl)cyclohexane, 1-(5-isoquinolinesulfonyl)homopiperazine and a pharmacologically acceptable salt thereof are preferably used since they are particularly superior in the promotion of adhesion of corneal endothelial cells. As the salt of the compound, a pharmaceutically acceptable acid addition salt is preferable. Examples of the acid include inorganic acids such as hydrochloric acid, hydrobromic acid, sulfuric acid and the like, organic acids such as methanesulfonic acid, fumaric acid, maleic acid, mandelic acid, citric acid, tartaric acid, salicylic acid and the like. More preferred are (+)-trans-4-(1-aminoethyl)-1-(4-pyridylcarbamoyl)cyclohexane 2 hydrochloride and 1-(5-isoquinolinesulfonyl) homopiperazine hydrochloride.

In the present invention, examples of the "promotion of adhesion of corneal endothelial cells" include both promotion of adhesion between corneal endothelium cells and promotion of adhesion of corneal endothelial cells to a culture substrate.

The adhesion promoter of the present invention provides an adhesion promoting action on corneal endothelial cells separated from a corneal tissue derived from a mammal (e.g., human, mouse, rat, hamster, rabbit, cat, dog, bovine, sheep, monkey etc.) or corneal endothelial cells separated therefrom and passaged. Since the adhesion promoter of the present invention is superior in an adhesion promoting action of corneal endothelial cells derived from human, which are considered to be particularly difficult to culture and passage, human-derived corneal endothelial cell is a preferable target.

Corneal endothelial cell plays a role of maintaining transparency of the cornea. When the density of the endothelial cells decreases over a certain limit, the cornea develops swelling and becomes incapable of maintaining transparency, whereby corneal endothelial dysfunction is developed. The adhesion promoter of the present invention promotes adhesion of corneal endothelial cells, enables formation of a corneal endothelial cell layer having good cell morphology and high cell density, and further shows an apoptosis suppressive action on corneal endothelial cells. Therefore, it is useful as a therapeutic agent or prophylactic agent for a disease accompanied by corneal endothelial dysfunction, such as bullous keratopathy and corneal endotheliitis. In addition, the adhesion promoter of the present invention is useful as a therapeutic agent or prophylactic agent for corneal endothelial dysfunction associated with intraocular surgery such as cataract surgery, vitreous surgery and the like, corneal endothelial dysfunction caused by increased intraocular pressure (particularly glaucomatous attack), or corneal endothelial dysfunction caused by insufficient oxygen due to contact lenses.

While the adhesion promoter of the present invention is not particularly limited as long as it has a dosage form suitable for topical administration to the eye, it is preferably formulated in the form of an intracameral injection or intraocular perfusion fluid. They can be prepared using conventional techniques widely used in the field. When it is topically administered to the eye in the form of an intracameral injection or intraocular perfusion fluid, the Rho kinase inhibitor and the corneal endothelial cells come into contact in the body, and adhesion of the corneal endothelial cells is promoted.

For example, when the adhesion promoter of the present invention is used as an intracameral injection or intraocular perfusion fluid, stabilizer (e.g., sodium bisulfite, sodium thiosulfate, sodium edetate, sodium citrate, ascorbic acid, dibutylhydroxytoluene etc.), solubilizer (e.g., glycerol, propylene glycol, macrogol, polyoxyethylene hydrogenated castor oil etc.), suspending agent (e.g., polyvinylpyrrolidone, hydroxypropylmethylcellulose, hydroxymethylcellulose, carboxymethylcellulose sodium etc.), emulsifier (e.g., polyvinylpyrrolidone, soybean lecithin, egg-yolk lecithin, polyoxyethylene hydrogenated castor oil, polysorbate 80 etc.), buffer agent (e.g., phosphate buffer, acetate buffer, borate buffer, carbonate buffer, citrate buffer, Tris buffer, glutamic acid, epsilon-aminocaproic acid etc.), thickening agent (e.g., water-soluble cellulose derivative such as methylcellulose, hydroxyethylcellulose, hydroxypropylmethylcellulose, carboxymethylcellulose etc., sodium chondroitin sulfate, sodium hyaluronate, carboxyvinyl polymer, polyvinyl alcohol, polyvinylpyrrolidone, macrogol etc.), preservative (e.g., benzalkonium chloride, benzethonium chloride, chlorhexidine gluconate, chlorobutanol, benzyl alcohol, sodium dehydroacetate, p-hydroxybenzoic esters, sodium edetate, boric acid etc.), isotonicity agent (e.g., sodium chloride, potassium chloride, glycerol, mannitol, sorbitol, boric acid, glucose, propylene glycol etc.), pH adjuster (e.g., hydrochloric acid, sodium hydroxide, phosphoric acid, acetic acid etc.), algefacient (e.g., 1-menthol, d-camphor, d-borneol, peppermint oil etc.) and the like can be added as additives. The amount of these additives to be added varies depending on the kind and use of the additive, and the like, and may be added at a concentration capable of achieving the object of the additive.

The amount of the active ingredient in the adhesion promoter of the present invention is generally 0.00001-1 w/v %, preferably 0.00001-0.1 w/v %, more preferably 0.0001-0.01 w/v %. While the dose and administration frequency vary depending on the symptom, age, body weight and administration form, when it is used as an intracameral injection to an adult, for example, a preparation containing 0.0001-0.1 w/v %, preferably 0.0001-0.01 w/v %, of an active ingredient can be generally administered several times, preferably 1-2 times, more preferably 1 time, per day, by 0.01-0.1 mL per administration.

The adhesion promoter of the present invention can also be added to a culture medium when corneal endothelial cells are cultured in a test tube. When culture is continued by adding a Rho kinase inhibitor to the culture medium, the Rho kinase inhibitor and the corneal endothelial cells come into contact in vitro, and adhesion of the corneal endothelial cells is promoted.

The present invention provides a culture medium for corneal endothelial cells, which contains a Rho kinase inhibitor. The Rho kinase inhibitor contained in the culture medium of the present invention is as described above.

The culture medium of the present invention can contain a medium generally used for culture of endothelial cells (e.g., DMEM (GIBCO BRL), serum (e.g., fetal bovine serum (FBS)), a growth factor (e.g., b-FGF), an antibiotic (e.g., penicillin, streptomycin) and the like.

The concentration of the Rho kinase inhibitor in the culture medium of the present invention is generally 1-100 μM, preferably 5-20 μM, more preferably 10 μM.

The culture medium of the present invention prevents shedding of cells by increasing adhesion of corneal endothelial cells, and enables formation of a corneal endothelial cell layer having good cell morphology and high cell density. Therefore, it can be preferably used for the below-mentioned production method of a corneal endothelial preparation of the present invention. In addition, the culture medium of the present invention is also used for maintaining corneal endothelial cells.

The present invention provides a corneal preservation solution containing a Rho kinase inhibitor. The Rho kinase inhibitor contained in the corneal preservation solution of the present invention is as described above. A corneal preservation solution is a liquid used for preserving a corneal graft isolated from a donor until transplantation to a recipient.

Examples of the corneal preservation solution of the present invention include preservation solutions generally used for corneal transplantation (corneoscleral explant preservation solution (Optisol GS: registered trade mark), preservation solution for eyeball for corneal transplantation (EPII: registered trade mark)), saline, phosphate buffered saline (PBS) and the like, each of which contains a Rho kinase inhibitor.

The concentration of the Rho kinase inhibitor in the corneal preservation solution of the present invention is generally 1-100 μM, preferably 5-20 μM, more preferably 10 μM.

The corneal preservation solution of the present invention prevents shedding of cells by increasing adhesion of corneal endothelial cells, and enables formation of a corneal endothelial cell layer having good cell morphology and high cell density. Therefore, it can be used as a corneal preservation solution used for organ transplantation and the like. In addition, the preservation solution of the present invention is also used as a preservation solution for cryopreservation of corneal endothelial cells. For cryopreservation, glycerol, dimethyl sulfoxide, propylene glycol, acetamide and the like may be further added to the preservation solution of the present invention.

The present invention provides a method of producing a corneal endothelial preparation, containing a step of culturing corneal endothelial cells using the culture medium of the present invention.

The corneal endothelial preparation characteristically contains a substrate and a corneal endothelial cell layer on the substrate, which has been cultured in a test tube.

In the present invention, the substrate is not particularly limited as long as it can support a cultured corneal endothelial cell layer and can maintain its shape in the body for at least 3 days after transplantation. In addition, the substrate may have a role of scaffold when culturing corneal endothelial cells in a test tube, or may only play a role of supporting the corneal endothelial cell layer after culture. Preferably, the substrate is used for culturing corneal endothelial cells, and has a role as scaffold which can be directly used for transplantation after completion of the culture.

Examples of the aforementioned substrate include polymer materials derived from naturally occurring substances such as collagen, gelatin, cellulose and the like, synthetic polymer materials such as polystyrene, polyester, polycarbonate, poly(N-isopropylacrylamide) and the like, biodegradable polymer materials such as polylactic acid, polyglycolic acid and the like, hydroxyapatite, amniotic membrane and the like.

While the shape of the aforementioned substrate is not particularly limited as long as it supports a corneal endothelial cell layer and is suitable for transplantation, it is preferably a sheet. When the preparation of the present invention is a sheet, it can be used after cutting into a size suitable for the application site during transplantation. It is also possible to roll up a small sheet and insert it from the lip of a wound. Preferable specific examples include a circular shape covering about 80% of a disordered corneal endothelial area. It is also preferable to form slits in the neighboring part of the aforementioned circle, so that it can be closely adhered to the application site.

In a preferable embodiment, the aforementioned substrate is collagen. As the collagen, the collagen sheet described in JP-A-2004-24852 can be preferably used. Such collagen sheet can be prepared according to the method described in the aforementioned JP-A-2004-24852 from, for example amniotic membrane.

The aforementioned corneal endothelial cell layer preferably shows at least one of the following characteristics. More preferably, it shows two or more, more preferably all, of the following characteristics.

(1) The cell layer has a single layer structure. This is one of the characteristics of the corneal endothelial cell layer in the body.

(2) The cell layer has a cell density of about 1,000-about 4,000 cells/mm$^2$. Particularly, when an adult is a recipient (transplant recipient), it is preferably about 2,000-about 3,000 cells/mm$^2$.

(3) The cell constituting the cell layer has a substantially hexagonal planar view. This is one of the characteristics of the cell constituting the corneal endothelial cell layer in the body. The preparation of the present invention is similar to the corneal endothelial cell layer in the body, exhibits function similar to that of inborn corneal endothelial cell layer, and can also exhibit in vivo proliferative capacity.

(4) Cells are regularly arranged in the cell layer. In the corneal endothelial cell layer in the body, the cells constituting the layer are regularly arrayed, due to which corneal endothelial cells are considered to maintain normal function and high transparency and the cornea is considered to appropriately exhibit water control function. Therefore, the preparation of the present invention having such morphological characteristics is expected to show a function similar to that of a corneal endothelial cell layer in the body.

The production method of the present invention includes a step of culturing corneal endothelial cells using the culture medium of the present invention and, for example, can be performed by the following method.

<1> Collection of Corneal Endothelial Cells and Culture in Test Tube

Corneal endothelial cells are collected from the cornea of the recipient himself/herself or a suitable donor by a conventional method. In consideration of the transplantation conditions in the present invention, allogenic corneal endothelial cells may be prepared. For example, Descemet's membrane and the endothelial cell layer of the corneal tissue are detached from the corneal stroma, placed in a culture dish, and treated with dispase and the like. By this process, corneal endothelial cells are removed from the Descemet's membrane. Corneal endothelial cells remaining on the Descemet's membrane can be removed by pipetting and the like. After removal of the Descemet's membrane, the corneal endothelial cells are cultured in the culture medium of the present invention. A culture medium can be obtained, for example, by appropriately adding FBS (fetal bovine serum), b-FGF (basic-fibloblast growth factor), and antibiotics such as penicillin, streptomycin and the like to commercially available DMEM (Dulbecco's Modified Eagle's Medium), and further adding Y-27632 or fasudil thereto. A culture container (culture dish) with a coating of type I collagen, type IV collagen, fibronectin, laminin or extracellular matrix of bovine corneal endothelial cell, and the like on the surface is preferably used. Alternatively, a general culture container treated with a commercially available coating agent such as FNC coating mix (registered trade mark) and the like may be used. By a combined use of such coating and the culture medium of the present invention, adhesion of corneal endothelial cells to the surface of a culture container is promoted, and good growth is made.

While the temperature conditions for culture of corneal endothelial cells are not particularly limited as long as the corneal endothelial cells grow, for example, the temperature is about 25-about 45° C., preferably about 30-about 40° C. in consideration of the growth efficiency, and further preferably about 37° C. The culture method is performed in a conventional cell culture incubator under humidification in the environment of about 5-10% $CO_2$ concentration.

<2> Passage Culture

Passage culture can be performed after growth of the corneal endothelial cells subjected to culture. Passage culture is preferably performed when the cells have reached subconfluent or confluent. Passage culture can be performed as follows. The cells are detached from the surface of a culture container by a treatment with trypsin-EDTA etc., and recovered. The culture medium of the present invention is added to the recovered cells to give a cell suspension. A centrifugation treatment is preferably performed during recovery of the cells or after recovery. Such a centrifugation treatment affords a cell suspension having a high cell density. Preferable cell density is about 1-2×$10^6$ cells/mL. As the conditions for the centrifugation treatment here, for example, 500 rpm (30 g)-1000 rpm (70 g), 1-10 min can be mentioned.

The cell suspension is seeded on a culture container in the same manner as in the above-mentioned initial culture, and cultured. While the dilution ratio during passage varies depending on the condition of cells, it is about 1:2-1:4, preferably about 1:3. The passage culture can be performed under culture conditions similar to those of the above-mentioned initial culture. While the culture time varies depending on the condition of cells to be used, it is, for example, 7-30 days. The above passage culture can be performed plural times as necessary. Using the culture medium of the present invention, cell adhesion in the early stages of culture is increased, whereby the culture time can be shortened.

<3> Preparation of Corneal Endothelial Cell Layer

A cell suspension is seeded on a substrate such as a collagen sheet and the like, and cultured. Here, the number of seeded cells is controlled such that the finally-produced corneal endothelial preparation has a cell layer having a desired cell density. To be precise, cells are seeded such that a cell layer having a cell density of about 1,000-about 4,000 cells/$mm^2$ is formed. Culture can be performed under conditions similar to those of the above-mentioned initial culture and the like. While the culture time varies depending on the condition of cells to be used, it is, for example, 3-30 days.

By culturing in the manner above, a corneal endothelial preparation wherein a corneal endothelial cell layer cultured in a test tube is formed on a substrate can be obtained.

In the present invention, the corneal endothelial preparation may contain the culture medium of the present invention so as to maintain corneal endothelial cells. In addition, the corneal endothelial preparation may contain the corneal preservation solution of the present invention until it is used for transplantation. The present invention also provides a combination of a corneal endothelial preparation and the culture medium or preservation solution of the present invention.

The corneal endothelial preparation obtained by the production method of the present invention can be used as a graft for the treatment of a disease requiring transplantation of corneal endothelium, for example, bullous keratopathy, corneal edema, corneal leukoma, particularly, bullous keratopathy caused by corneal endothelial dysfunction due to corneal dystrophy, trauma or intraocular surgery.

The subject of administration of the adhesion promoter and corneal endothelial preparation of the present invention includes, for example, a mammal (e.g., human, mouse, rat, hamster, rabbit, cat, dog, bovine, sheep, monkey etc.).

EXAMPLES

The present invention is explained in more detail in the following by referring to Examples, which are not to be construed as limitative. The experimental animals were used according to the International Guiding Principles for Biomedical Research Involving Animals, as well as Act on welfare and management of animals, and standard relating to feeding, keeping and the like of experimental animals. This experiment was performed according to Guidelines of the Association for Research in Vision and Ophthalmology on the Use of Animals in Ophthalmic and Vision Research.

Example 1

Figure 2:
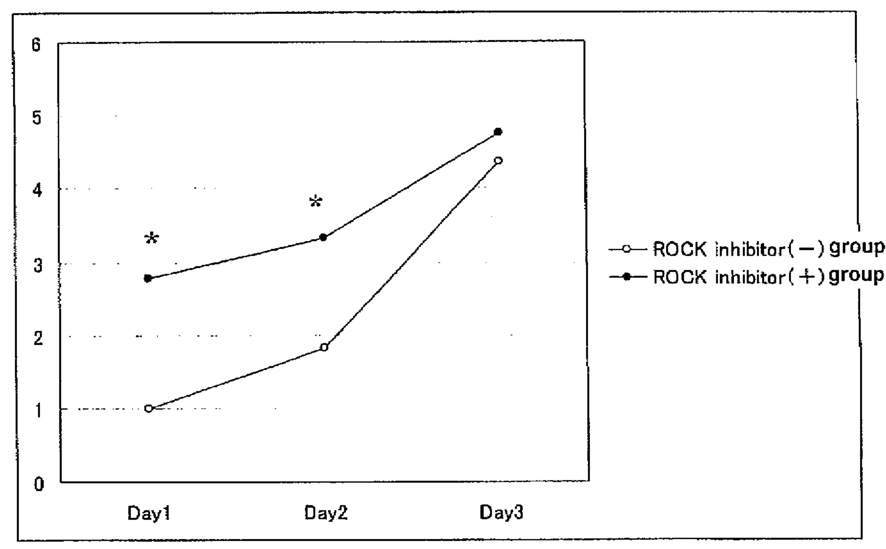
FIG. 2 is a graph showing the growth of the primary culture of rabbit corneal endothelial cells as examined by MTS assay, wherein the vertical axis shows the value relative to the absorbance of Rock inhibitor (−) group on day 1.

Study of Influence of ROCK Inhibitor on Culture of Rabbit Corneal Endothelial Cell From a rabbit corneal tissue isolated immediately after euthanasia, Descemet's membrane with corneal endothelial cells attached thereto was separated. The Descemet's membrane was incubated together with Dispase II (1.2 U/ml, Roche Applied Science) under the conditions of 37° C., 5% $CO_2$ for 45 min, and the corneal endothelial cells were mechanically separated by a pipetting operation. The separated corneal endothelial cells were centrifuged, the cells of a ROCK inhibitor(+) group were stirred in a medium for corneal endothelium added with Y-27632 (10 μM) and the cells of a ROCK inhibitor(−) group were stirred in a medium for corneal endothelium without addition of Y-27632, to the same concentration, and the cells were seeded on a 96 well plate at a density of about 2000 cells per well. As a medium for corneal endothelium, a culture medium (DMEM, Gibco Invitrogen) added with 1% fetal bovine serum and 2 mg/ml bFGF (Gibco Invitrogen) was used. The plate was pre-treated with an FNC coating mix (Athena ES) for 10 min. At 72 hr from the start of the culture, the culture medium was exchanged and, after 72 hr, both the ROCK inhibitor(+) group and ROCK inhibitor(−) group were cultured in a normal medium for corneal endothelium free of Y-27632 until day 5. The phase contrast photomicrograph of the primary culture of rabbit corneal endothelial cells after 24 hr from the start of the culture is shown in FIG. 1. From day 1 to day 3 after the start of the culture, the cells were counted every 24 hr by MTS ([3-(4,5-dimethylthiazol-2-yl)-5-(3-carboxymethoxyphenyl)-2-(4-sulfophenyl)-2H-tetrazolium]) assay using CellTiter 96 (registered trade mark) AQueous One Solution Cell Proliferation (Promega) (FIG. 2).

Figure 3:
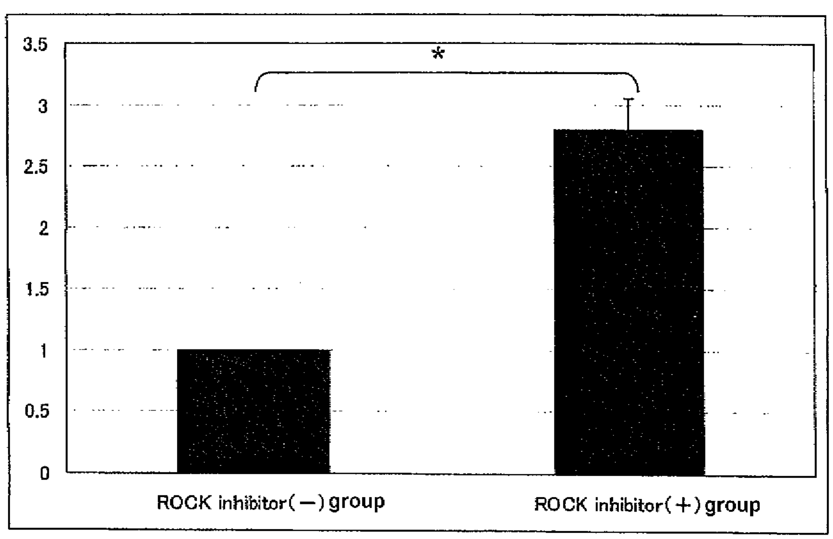
FIG. 3 is a graph showing the adhesion of the primary culture of rabbit corneal endothelial cells after 24 hr from the start of the culture, wherein the vertical axis shows the value relative to the absorbance of Rock inhibitor (−) group after 24 hr from the start of the culture.

In the ROCK inhibitor(+) group (FIG. 1B), the cell adhesion in 24 hr (day 1) after cell seeding significantly increased to about 2.8-fold (FIGS. 2 and 3) as compared to the ROCK inhibitor(−) group (FIG. 1A). At day 3 when the cells reached confluent, a significant difference was not found between the two groups (FIG. 2). Therefrom it was clarified that Y-27632 has an action to increase cell adhesion in the early stages after passage in the primary culture of rabbit corneal endothelial cells. In addition, similar results were also obtained in the study using a passage culture of rabbit corneal endothelial cells, and therefore, Y-27632 was considered to act on the cell adhesion in early stages after passage in the primary culture and passage culture.

Example 2

Study of Influence of Y-27632 on Culture of Monkey Corneal Endothelial Cell

From the corneal tissue isolated from Macaca fascicularis euthanized for other purpose, Descemet's membrane with corneal endothelial cells attached thereto was separated. For the ROCK inhibitor(+) group, the Descemet's membrane was placed in a medium for corneal endothelium added with Y-27632 (10 μM) and incubated under the conditions of 37° C., 5% $CO_2$ for 10 min. For the ROCK inhibitor(−) group, the membrane was placed in a medium for corneal endothelium without addition of Y-27632 and incubated for 10 min under the same conditions. As the medium for corneal endothelium, the same cell culture medium as in Example 1 was used. The Descemet's membrane after the incubation was incubated together with Dispase II (1.2 U/ml, Roche Applied Science) under the conditions of 37° C., 5% $CO_2$ for 45 min, and the corneal endothelial cells were mechanically separated by a pipetting operation. The separated corneal endothelial cells were centrifuged and stirred in the media for corneal endothelium with Y-27632(+) and Y-27632(−) to the same concentration, and the cells were seeded on a 12 well plate at a density of about 20000 cells per well. The plate was pre-treated with an FNC coating mix (Athena ES) for 10 min. At 72 hr from the start of the culture, the culture medium was exchanged and, after 72 hr, both the ROCK inhibitor(+) group and ROCK inhibitor(−) group were cultured in a normal medium for corneal endothelium free of Y-27632.

Figure 4:
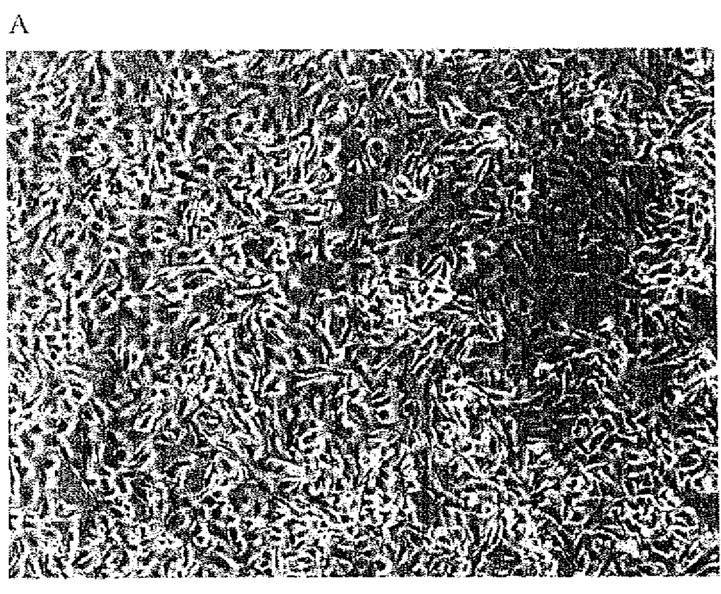
FIG. 4 is a phase contrast photomicrograph of the primary culture of monkey corneal endothelial cells on day 3 from the start of the culture, wherein the magnification is 100-fold.
Figure 4:
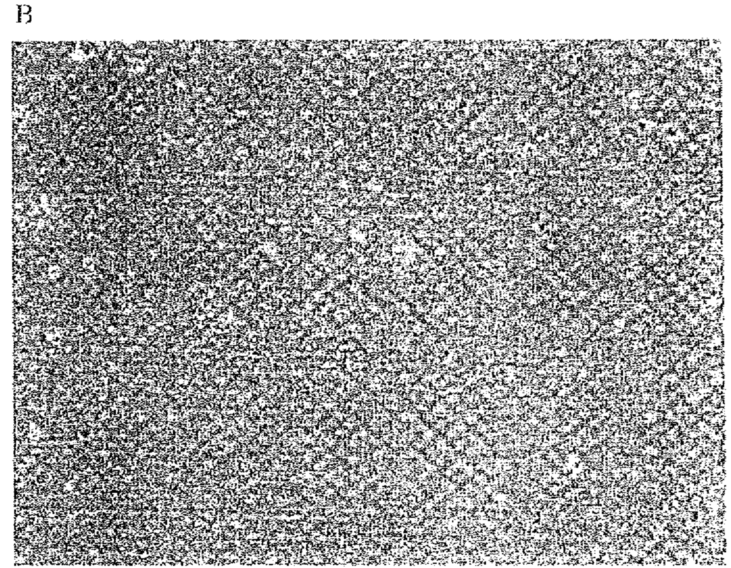

From FIG. 4, in the primary culture of Macaca fascicularis corneal endothelial cells after 24 hr from the start of the culture, apparently more cells were adhered onto the plate in the ROCK inhibitor(+) (FIG. 4B) as compared to ROCK inhibitor(−) (FIG. 4A). The number of days before reaching confluent was 3 for the ROCK inhibitor(+), whereas it was 7 for ROCK inhibitor(−). Therefrom it was shown that Y-27632 increases cell adhesion in the early stages after the start of the culture and is a useful drug that enables cell culture even in monkey corneal endothelial cells considered to be difficult for culture outside the body as compared to rabbit.

Example 3

Study of Influence of Y-27632 on Culture of Human Corneal Endothelial Cell

Of human corneal tissues obtained from the US eye bank, the central part (diameter 7 mm) had been used for corneal transplantation and the remaining surrounding corneal tissue was used. The Descemet's membrane with corneal endothelial cells adhered thereto was separated. For the ROCK inhibitor(+) group, the Descemet's membrane was placed in a medium for corneal endothelium added with Y-27632 (10 μM) and incubated under the conditions of 37° C., 5% $CO_2$ for 10 min. For the ROCK inhibitor(−) group, the membrane was placed in a medium for corneal endothelium without addition of Y-27632 and incubated for 10 min under the same conditions. As the medium for corneal endothelium, the same culture medium as in Example 1 was used. The Descemet's membrane after the incubation was incubated together with Dispase II (1.2 U/ml, Roche Applied Science) under the conditions of 37° C., 5% $CO_2$ for 45 min, and the corneal endothelial cells were mechanically separated by a pipetting operation. The separated corneal endothelial cells were centrifuged and stirred in the media for corneal endothelium with Y-27632(+) and Y-27632(−) to the same concentration, and the cells were seeded on a 48 well plate pre-treated with an FNC coating mix (Athena ES) at a density of about 10000 cells per well. The number of human corneal endothelial cells obtained from the surrounding corneal tissue was extremely small, and therefore, the donor cornea of one eye was cultured in one well. The donor corneas used for the study were: culture was started 6 days after death of the donor (age 69) for the ROCK inhibitor(+) group, and culture was started 7 days after death of the donor (age 51) for the ROCK inhibitor (−) group. An influence on the age and the time lapsed from the death of the donor to cell culture is considered to be almost the same.

At 72 hr from the start of the culture, the culture medium was exchanged and, after 72 hr, both the ROCK inhibitor(+) group and ROCK inhibitor(−) group were cultured in a normal medium for corneal endothelium free of Y-27632. To study influence on the cell adhesion in the early stages after the start of the culture and cell morphology, the cells were observed with a phase contrast microscope and photographs were taken with a digital camera after the start of the culture (FIG. 5).

Figure 5:
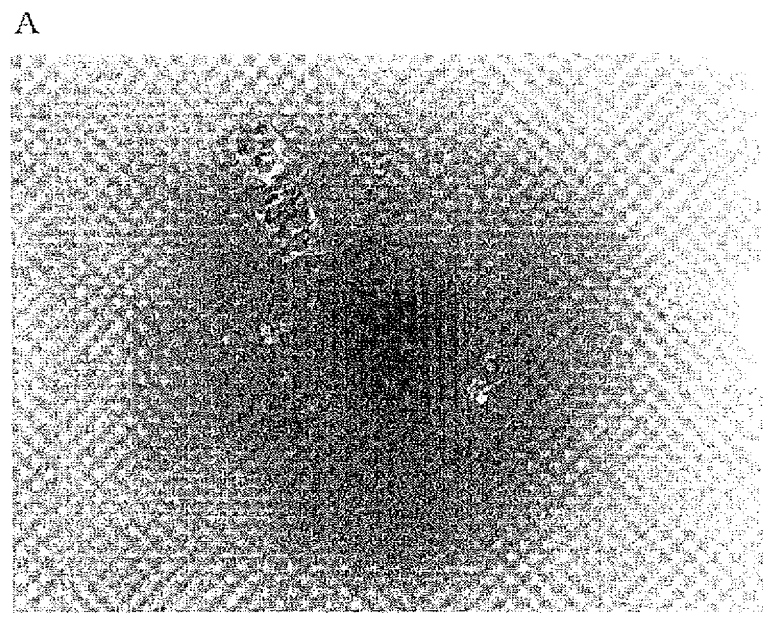
FIG. 5 is a phase contrast photomicrograph of the primary culture of human corneal endothelial cells (day 7, magnification: 100-fold).
Figure 5:
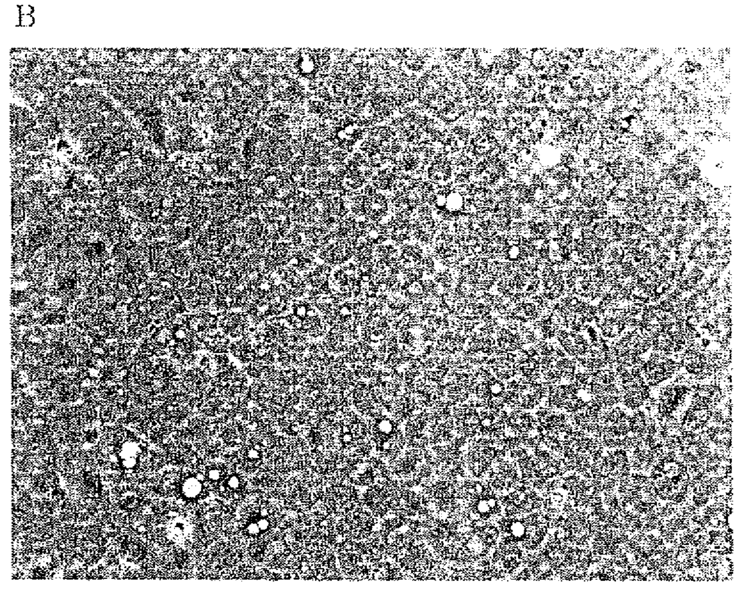

From FIG. 5, on day 7 after the start of the culture, a confluent and highly dense single cell layer consisting of cells (uniform polygonal cells) similar to normal corneal endothelial cells was formed in the ROCK inhibitor(+) group (FIG. 5B), whereas fibroblast-like elongated endothelial cells with low density only survived in an islet shape in the ROCK inhibitor(−) group (FIG. 5A). From these results, it is considered that, in the primary culture of human corneal endothelium known to be extremely difficult for culture, addition of Y-27632 having an action to increase cell adhesion in the early stages after the start of the culture to a culture medium enables formation of a corneal endothelial cell layer having good cell morphology and high cell density.

Formulation Example 1

Intracameral Injection Containing Rho Kinase Inhibitor

The following intracameral injection is prepared according to a conventional method.

| | |
|---|---|
| Y-27632 | 10 mg |
| sodium dihydrogen phosphate | 0.1 g |
| sodium chloride | 0.9 g |
| sodium hydroxide | e.q. |
| sterilization purified water | e.q. |
| total amount | 100 mL (pH 7) |

Y-27632 manufactured by Wako Pure Chemical Industries, Ltd is used.

Formulation Example 2

Intraocular Perfusion Fluid Containing Rho Kinase Inhibitor

The following intraocular perfusion fluid is prepared according to a conventional method.

| | |
|---|---|
| Y-27632 | 1.0 mg |
| OPEGUARD MA | e.q. |
| total amount | 100 mL |

OPEGUARD MA manufactured by Senju Pharmaceutical Co., Ltd., and Y-27632 manufactured by Wako Pure Chemical Industries, Ltd are used.

Formulation Example 3

Rho Kinase Inhibitor-Containing Culture Medium for Preparation of Corneal Endothelium Sheet The following culture medium is prepared according to a conventional method.

| | |
|---|---|
| Y-27632 | 0.5 mg |
| FBS | 10 mL |
| penicillin-streptomycin solution | 1 mL |

-continued

| | |
|---|---|
| FGF basic | 200 ng |
| DMEM | e.q. |
| total amount | 100 mL |

FBS manufactured by Invitrogen, penicillin-streptomycin solution manufactured by Nacalai Tesque (containing penicillin 5000 u/mL and streptomycin 5000 μg/mL), FGF basic manufactured by Invitrogen, Y-27632 manufactured by Wako Pure Chemical Industries, Ltd., and DMEM manufactured by Invitrogen are used.

Formulation Example 4

Corneal Preservation Solution Containing Rho Kinase Inhibitor

The following preservation solution is prepared according to a conventional method.

| | |
|---|---|
| Y-27632 | 0.2 mg |
| Optisol-GS | e.q. |
| total amount | 100 mL |

Optisol-GS manufactured by Bausch & Lomb, Inc., and Y-27632 manufactured by Wako Pure Chemical Industries, Ltd are used.

Example 4

Figure 6:
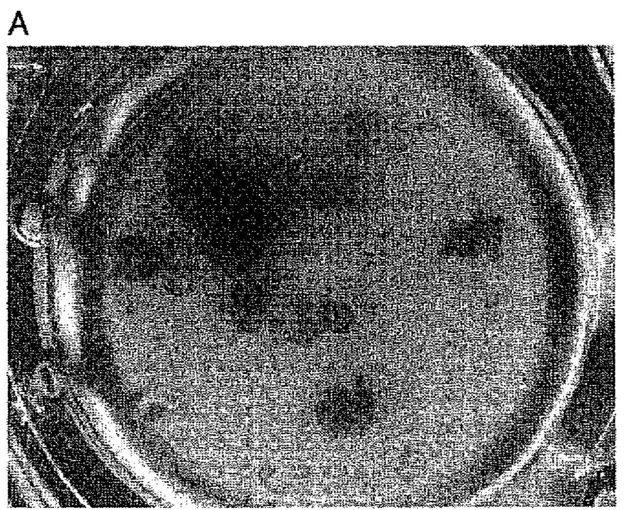
FIG. 6 shows a photograph of the primary culture of monkey corneal endothelial cells (A: ROCK inhibitor(−), B: ROCK inhibitor(+), magnification: 20-fold) and graph (C) showing the total area of cultured cells.
Figure 6:
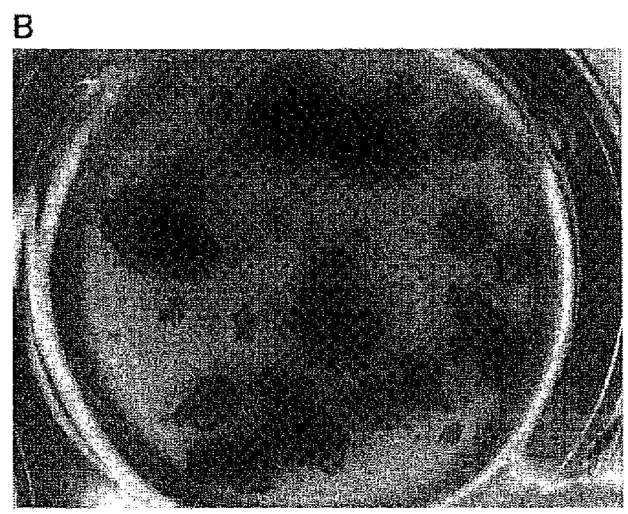

Study of Influence of Y-27632 on Primary Culture of Monkey Corneal Endothelial Cell From the corneal tissue isolated from Macaca fascicularis euthanized, Descemet's membrane with corneal endothelial cells attached thereto was separated. In the same manner as in Example 2, for the ROCK inhibitor(+) group, the Descemet's membrane was placed in a medium for corneal endothelium added with Y-27632 (10 μM) and incubated under the conditions of 37° C., 5% CO2 for 10 min. For the ROCK inhibitor(−) group, the membrane was placed in a medium for corneal endothelium without addition of Y-27632 and incubated for 10 min under the same conditions. As the medium for corneal endothelium, the same cell culture medium as in Example 1 was used. The Descemet's membrane after the incubation was incubated together with Dispase II (1.2 U/ml, Roche Applied Science) under the conditions of 37° C., 5% CO2 for 45 min, and the corneal endothelial cells were mechanically separated by a pipetting operation. The separated corneal endothelial cells were centrifuged and stirred in the media for corneal endothelium with Y-27632(+) and Y-27632(−) to the same concentration, and the cells were seeded on a 96 well plate at a density of about 2000 cells per well. At 72 hr from the start of the culture, the culture medium was exchanged and, after 72 hr, both the ROCK inhibitor(+) group and ROCK inhibitor(−) group were cultured in a normal medium for corneal endothelium free of Y-27632. On day 10 of culture, the cells were fixed with 4% para-formaldehyde at room temperature for 10 min, and stained with toluidine blue (FIGS. 6A and 6B). The total area of the cells was measured using Image J (National Institutes of Health) and analyzed (FIG. 6C).

In the primary culture of Macaca fascicularis corneal endothelial cells at day 10 after the start of the culture, the ROCK inhibitor(+) (FIG. 6B) significantly increased the total area of cultured cells to about 1.6-fold (FIG. 6C) as compared to the ROCK inhibitor(−) (FIG. 6A) by promoting adhesion in the early stages of culture. Therefrom it was shown that Y-27632 is a drug useful for primary culture even in monkey corneal endothelial cells considered to be difficult for culture outside the body.

Example 5

Study of Optimal Concentration of Y-27632 for Monkey Corneal Endothelial Cells

Figure 7:
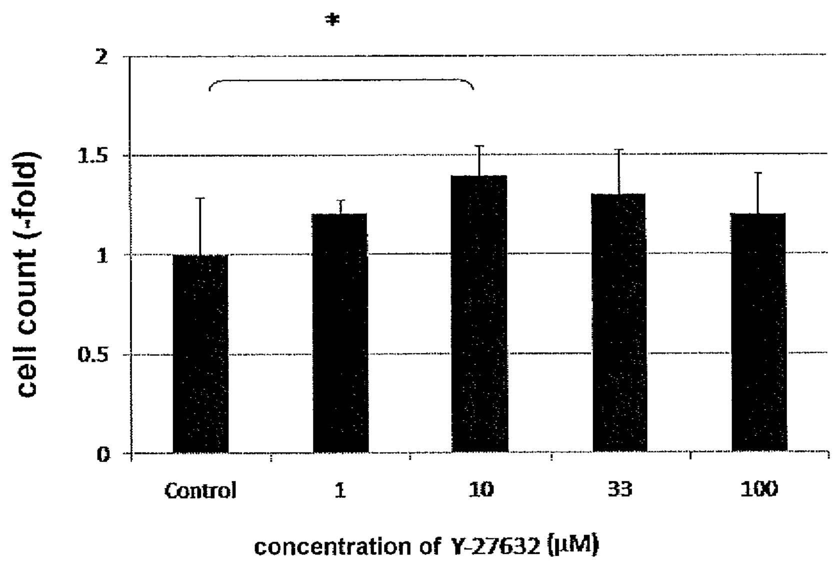
FIG. 7 is a graph showing the viable cell number of the primary culture of monkey corneal endothelial cells.

Monkey corneal endothelial cells (primary culture) collected in the same manner as in Example 2 were placed in media for corneal endothelium each added with Y-27632 at 1, 10, 33 and 100 μM and a medium for corneal endothelium without addition of Y-27632, and stirred to the same concentration, and the cells were seeded on a 96 well plate at a density of about 2000 cells per well. At 24 hr from the start of the culture, viable cells were counted using CellTiter-Glo (registered trade mark, Promega) (FIG. 7).

When the corneal endothelial cells at 24 hr from the start of the culture were cultured in a medium containing 10 μM Y-27632, the number of cells that adhered onto the plate was significantly high (FIG. 7) as compared to cell culture in a medium for corneal endothelium without addition of Y-27632 and a medium for corneal endothelium containing different concentrations of Y-27632. Therefrom, it was shown that Y-27632 at a concentration of 10 μM is most effective for monkey corneal endothelial cells.

Example 6

Figure 8:
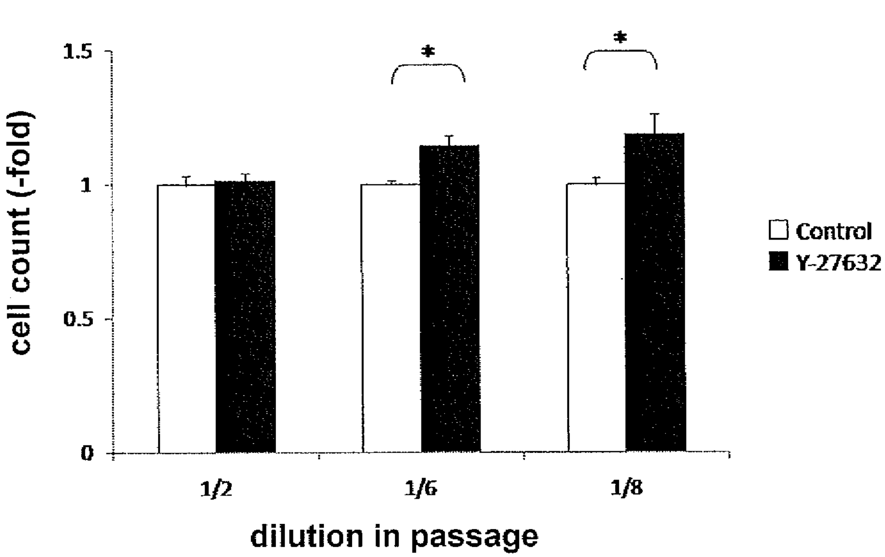
FIG. 8 is a graph showing an influence of Y-27632 on the passage culture of monkey corneal endothelial cells.

Study of Influence of Y-27632 on Passage Culture of Monkey Corneal Endothelial Cell From the corneal tissue isolated from Macaca fascicularis euthanized, Descemet's membrane with corneal endothelial cells attached thereto was separated. The Descemet's membrane was incubated together with Dispase II (1.2 U/ml, Roche Applied Science) under the conditions of 37° C., 5% $CO_2$ for 45 min, and the corneal endothelial cells were mechanically separated by a pipetting operation. The separated corneal endothelial cells were centrifuged and seeded on a media for corneal endothelium. The corneal endothelial cells that reached confluent were incubated with 0.05% trypsin under the conditions of 37° C., 5% $CO_2$ for 10 min, and passage-cultured. After 4 to 6 passages, the corneal endothelial cells were placed in a 96-well plate to a dilution of ½, ⅙ or ⅛. The passage culture was continued using a medium for corneal endothelium added with Y-27632 (10 μM) for the ROCK inhibitor(+) group and a medium for corneal endothelium without addition of Y-27632 for the ROCK inhibitor(−) group. At 24 hr after the passage, the cells were counted in the same manner as in Example 5 using CellTiter-Glo (registered trade mark, Promega) (FIG. 8).

When the cultured Macaca fascicularis corneal endothelial cells at 24 hr after the passage were passage-cultured in a medium containing Y-27632, the number of cells that adhered onto the plate was significantly high (FIG. 8) as compared to a medium for corneal endothelium without addition of Y-27632. Therefrom it was shown that Y-27632 was also effective for, in addition to primary culture, passage culture of monkey corneal endothelial cells.

Example 7

Figure 9:
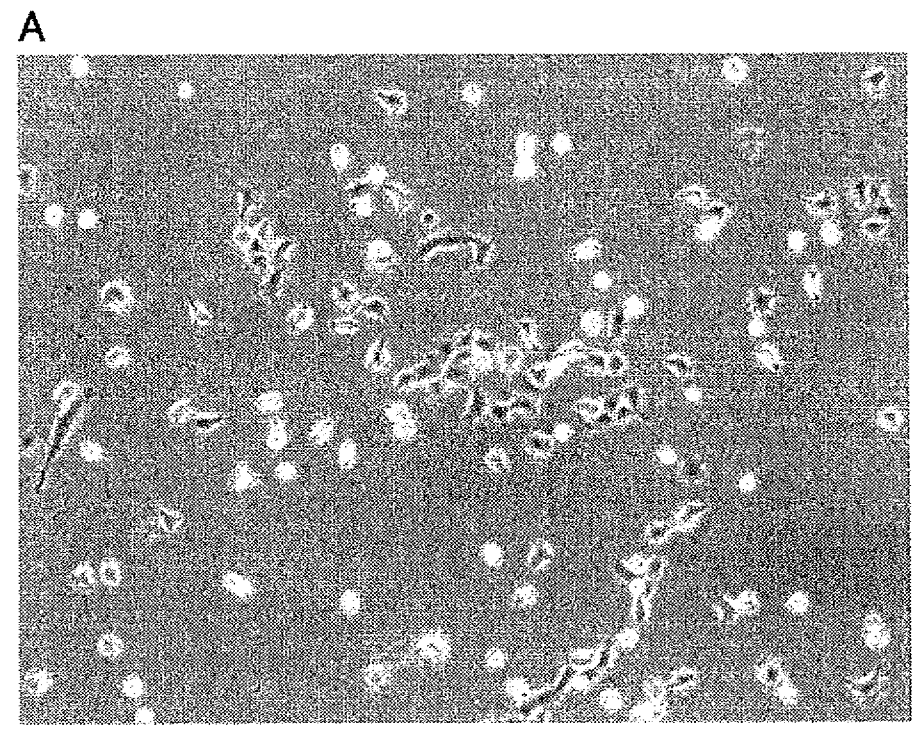
FIG. 9 is a phase contrast photomicrograph showing an influence of Y-27632 on the cell morphology during the passage culture of monkey corneal endothelial cells (magnification: 100-fold).
Figure 9:
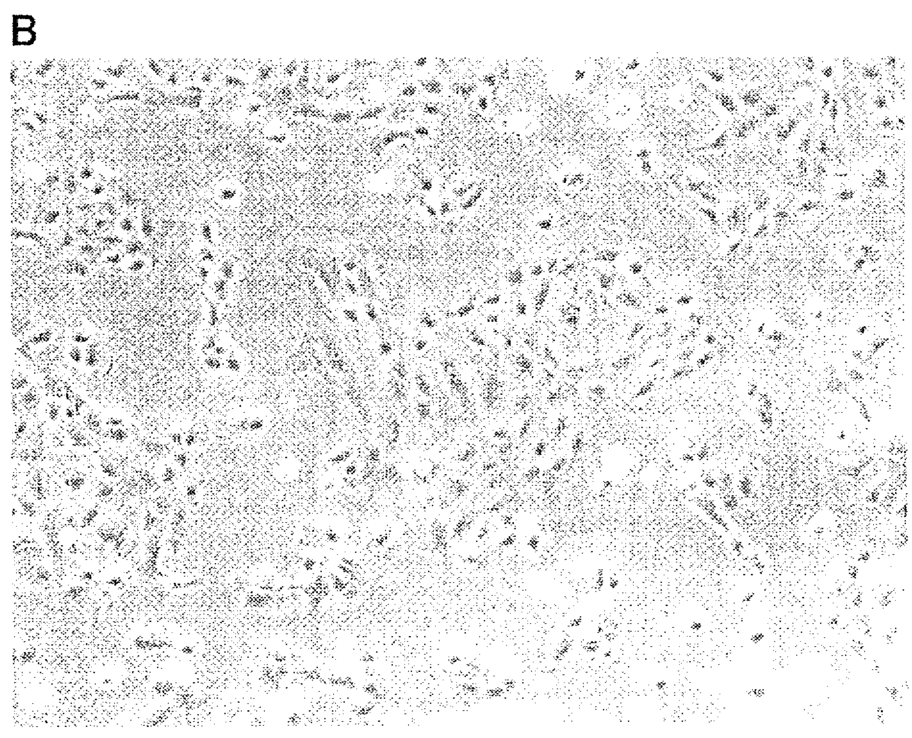
Figure 10:
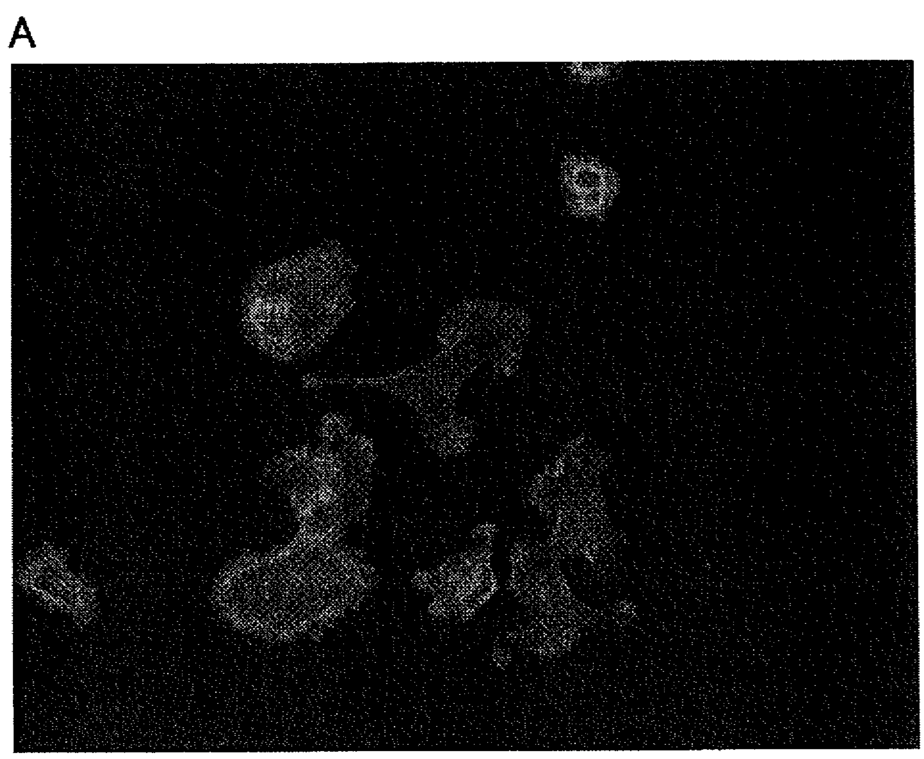
FIG. 10 is a photomicrograph showing an influence of Y-27632 on the cell morphology during the passage culture of monkey corneal endothelial cells (phalloidin fluorescence staining, magnification: 200-fold).
Figure 10:
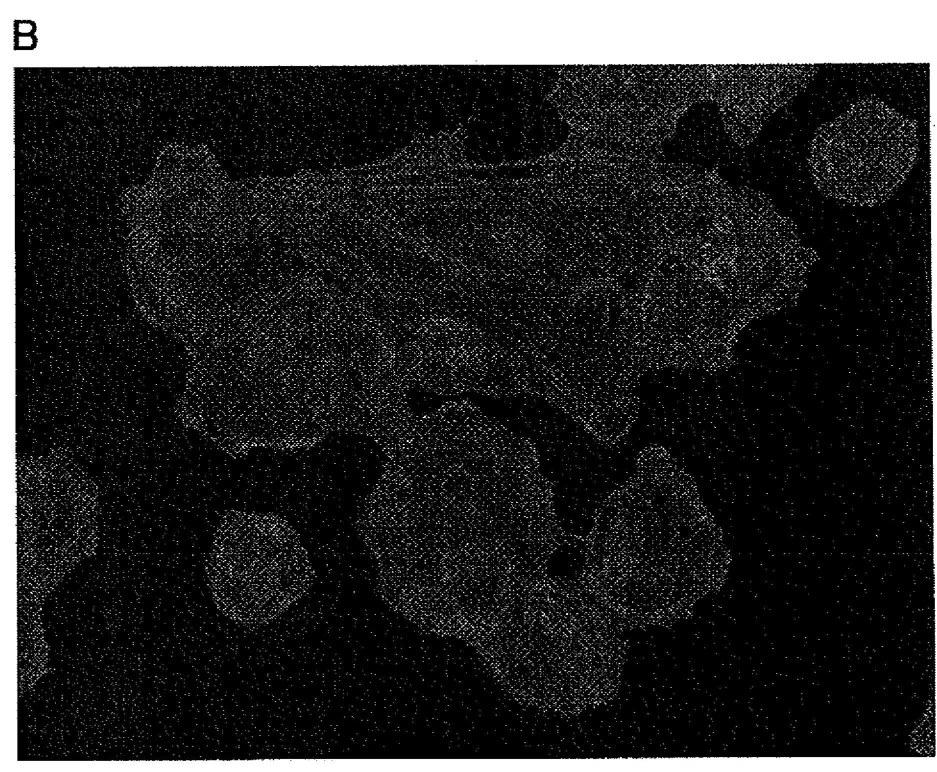

Study of Influence of Y-27632 on Cell Morphology in Passage Culture of Monkey Corneal Endothelial Cell The Macaca fascicularis corneal endothelial cells passage-cultured in the same manner as in Example 6 were subcultured on a slide glass to a dilution of ¼. At 24 hr from the passage culture, cell morphology was observed with a phase contrast microscope (FIGS. 9A and 9B). Furthermore, the corneal endothelial cells on the slide glass were fixed with 4% para-formaldehyde at room temperature for 10 min, and actin fiber was stained by phalloidin fluorescence staining (FIGS. 10A and 10B).

In the cultured Macaca fascicularis corneal endothelial cells at 24 hr after the passage, when the passage culture was performed in a medium containing Y-27632 (FIG. 9B), adhesion of the cells onto the slide glass increased, flattening to corneal endothelial cell-like cells was promoted, and aggregation of cells also increased as compared to a medium for corneal endothelium without containing Y-27632 (FIG. 9A). In addition, by phalloidin fluorescence staining, when the passage culture was performed in a medium containing Y-27632 (FIG. 10B), actin stress fiber was clearly observed as compared to a medium for corneal endothelium without containing Y-27632 (FIG. 10A), and it was found that Y-27632 promotes formation of cytoskeleton.

Example 8

Study of Influence of Y-27632 on Cell Cycle of Monkey Corneal Endothelial Cell

Figure 11:
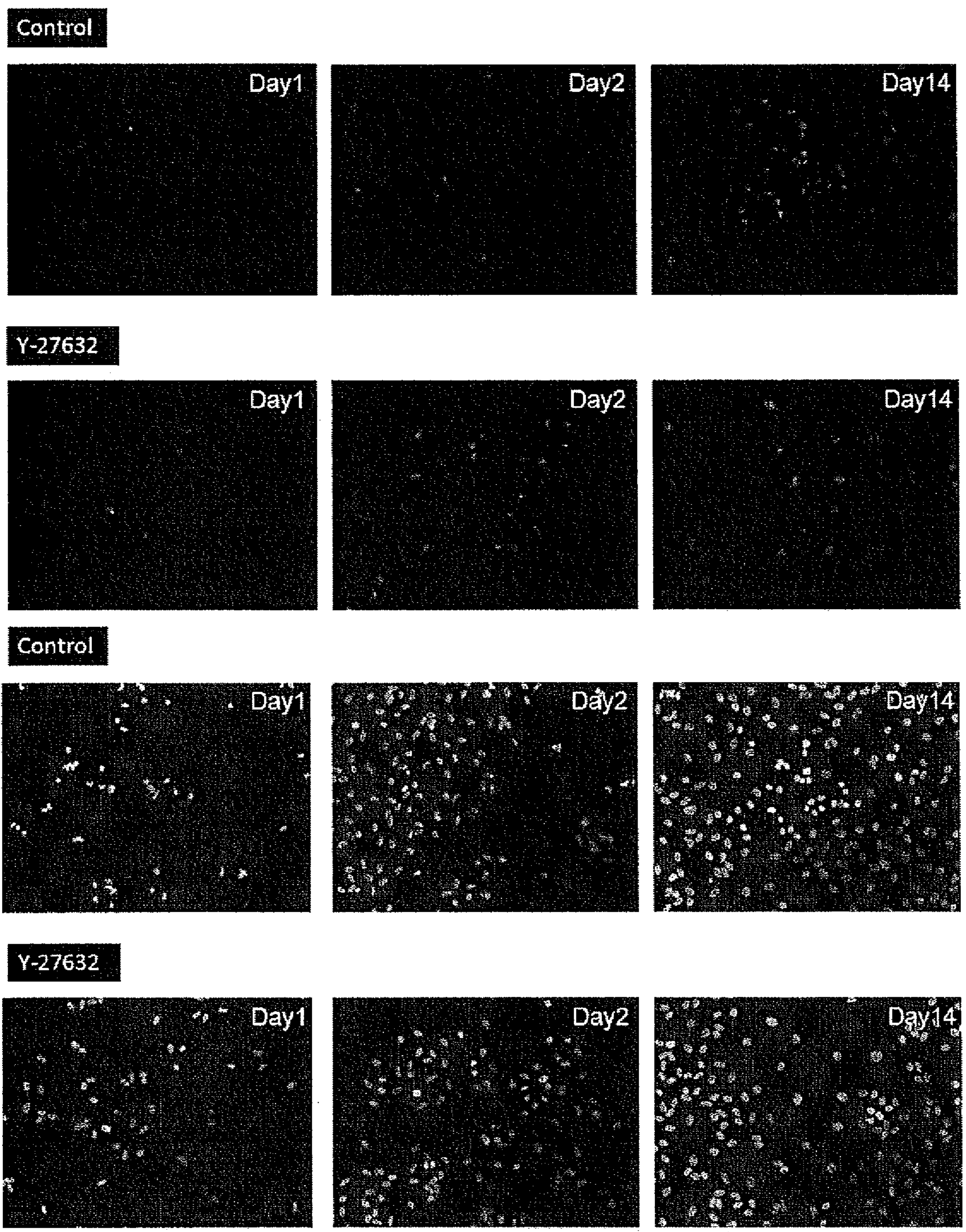
FIG. 11 is a photomicrograph showing an influence of Y-27632 on the cell cycle of monkey corneal endothelial cells (anti-Ki67 antibody staining, magnification: 200-fold).
Figure 12:
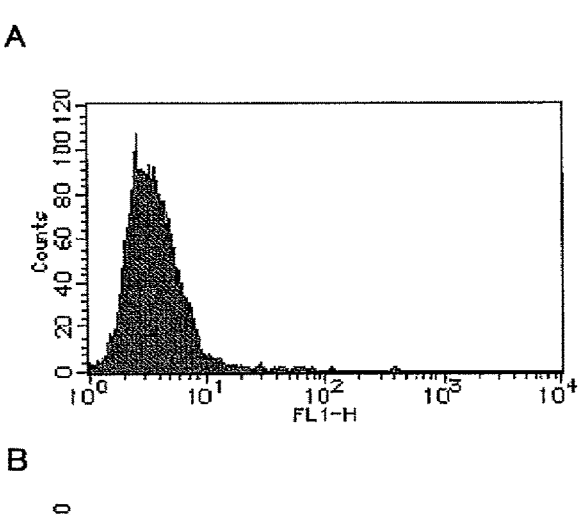
FIG. 12 shows the results of flow cytometry examining an influence of Y-27632 on the cell cycle of monkey corneal endothelial cells.
Figure 12:
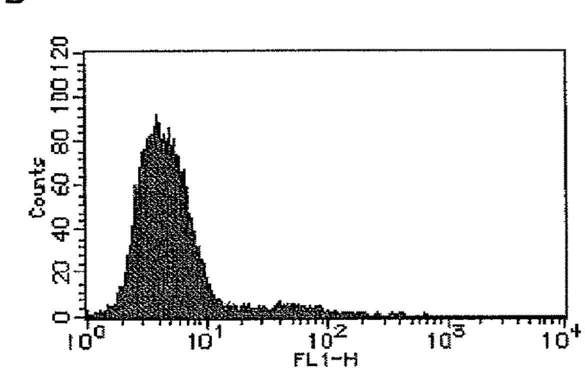
Figure 12:
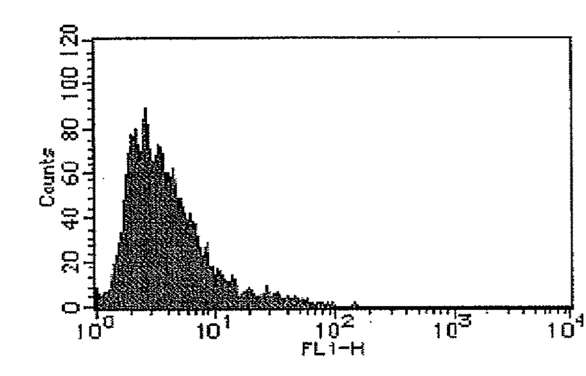
Figure 12:
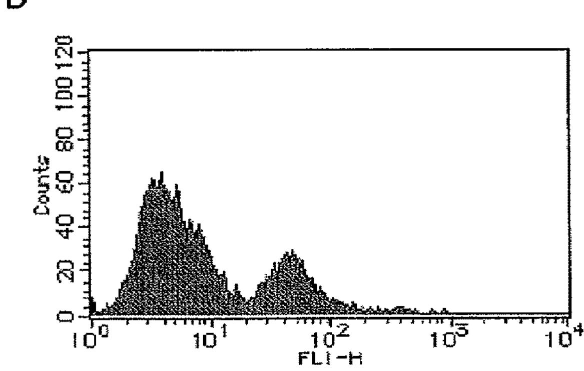
Figure 13:
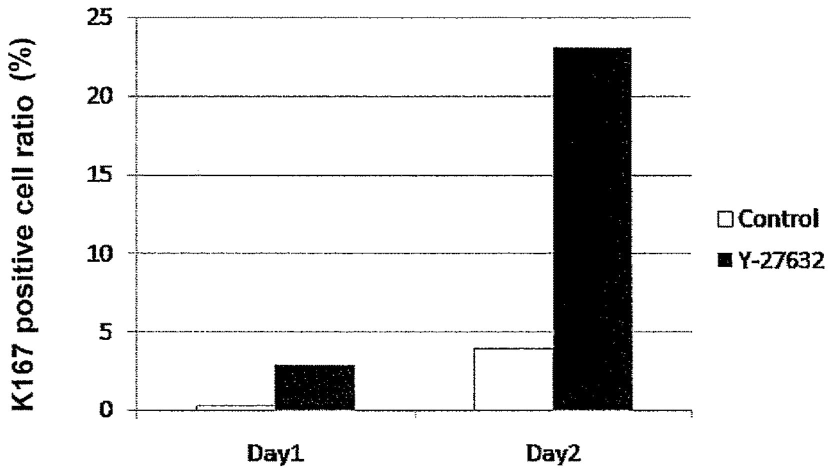
FIG. 13 is a graph showing the results of the flow cytometry of FIG. 12 by anti-Ki67 antibody positive cell rate.

The Macaca fascicularis corneal endothelial cells passage-cultured in the same manner as in Example 6 were subcultured on a slide glass to a dilution of ¼. A medium for corneal endothelium added with Y-27632 (10 μM) was used for the ROCK inhibitor(+) group and a medium for corneal endothelium without addition of Y-27632 was used for the ROCK inhibitor(−) group. On days 1, 2 and 14 of the passage culture, the corneal endothelial cells on the slide glass were fixed with 4% para-formaldehyde at room temperature for 10 min, and immunostained with anti-Ki67 antibody (FIG. 11). Similarly, moreover, the Macaca fascicularis corneal endothelial cells were passage-cultured to a dilution of ¼ in each of the ROCK inhibitor(+) group and ROCK inhibitor(−) group. On days 1 and 2 of the passage culture, the cells were collected using 0.05% trypsin and subjected to flow cytometry using anti-Ki67 antibody, and the cell cycle was examined (FIGS. 12 and 13).

As compared to the ROCK inhibitor(−) group, the ROCK inhibitor(+) group contained many Ki67 positive cells on days 1 and 2 of the passage culture. However, when the cells reached almost confluent on day 14, the number of positive cells of the ROCK inhibitor(+) group was less than that of the ROCK inhibitor(−) group (FIG. 11). Also in the flow cytometry, the ROCK inhibitor(+) group contained many Ki67 positive cells on days 1 and 2 of the passage culture as compared to the ROCK inhibitor(−) group (FIGS. 12 and 13).

Since Ki67 antigen is found in the cell nucleus in the cell proliferation cycle G1, and from S to M phases, it was shown that Y-27632 has an action to promote cell cycle in the early stages after the passage culture of Macaca fascicularis corneal endothelial cells and is a drug useful for efficient cell culture.

Example 9

Study of Influence of Y-27632 on Apoptosis of Monkey Corneal Endothelial Cell

Figure 14:
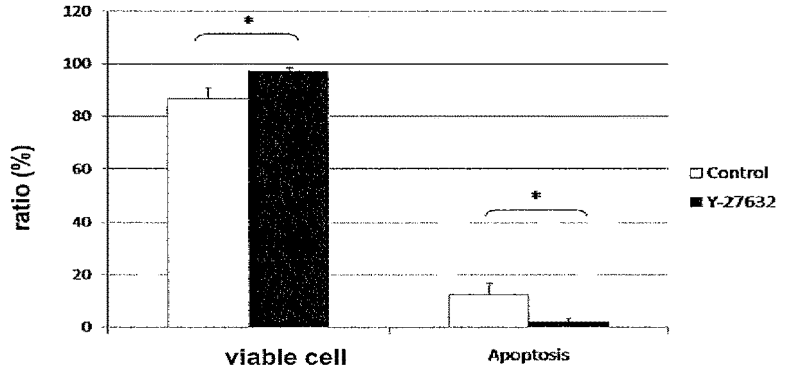
FIG. 14 is a graph showing an influence of Y-27632 on the apoptosis of monkey corneal endothelial cells.
Figure 15:
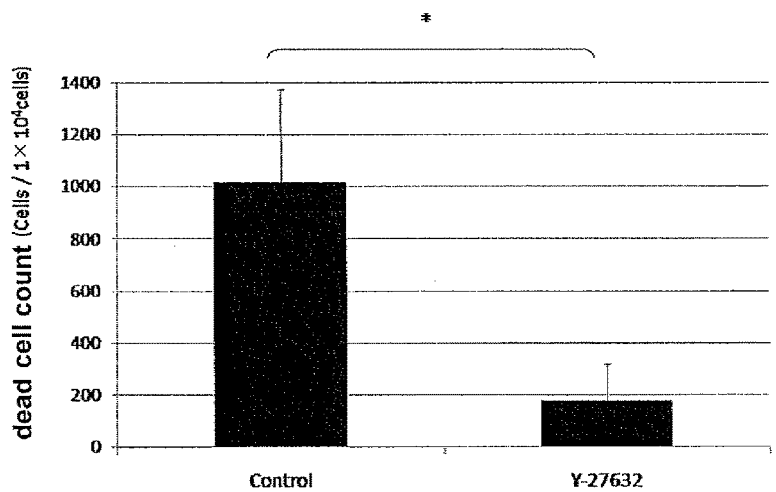
FIG. 15 is a graph showing an influence of Y-27632 on the apoptosis of monkey corneal endothelial cells by the number of dead cells.

The Macaca fascicularis corneal endothelial cells passage-cultured in the same manner as in Example 6 were subcultured to a dilution of ¼. A medium for corneal endothelium added with Y-27632 (10 μM) was used for the ROCK inhibitor(+) group and a medium for corneal endothelium without addition of Y-27632 was used for the ROCK inhibitor(−) group. On day 1 of the passage culture, all the cells including those in the medium were collected using 0.05% trypsin and subjected to flow cytometry using Annexin V and PI (Propidium Iodide), and apoptosis was examined (FIGS. 14 and 15).

The ROCK inhibitor(+) group showed a significant decrease in the ratio of apoptotic cells to the entire cells on day 1 of the passage culture (FIG. 14) as compared to the ROCK inhibitor(−) group. Furthermore, a comparison of the number of apoptotic cells per $1\times10^4$ cells revealed a significant decrease in the ROCK inhibitor(+) group as compared to the ROCK inhibitor(−) group (FIG. 15).

Therefrom it was shown that Y-27632 has an action to suppress apoptosis during passage culture of Macaca fascicularis corneal endothelial cells.

Example 10

Study of Influence of Y-27632 on Density of Monkey Corneal Endothelial Cell

From the corneal tissue isolated from Macaca fascicularis euthanized, Descemet's membrane with corneal endothelial cells attached thereto was separated. The Descemet's membrane was incubated together with Dispase II (1.2 U/ml, Roche Applied Science) under the conditions of 37° C., 5% $CO_2$ for 45 min, and the corneal endothelial cells were mechanically separated by a pipetting operation. The separated corneal endothelial cells were centrifuged and seeded on a medium for corneal endothelium. The corneal endothelial cells that reached confluent were incubated with 0.05% trypsin under the conditions of 37° C., 5% $CO_2$ for 10 min, and passage-cultured. A medium for corneal endothelium added with Y-27632 (10 μM) was used for the ROCK inhibitor(+) group and a medium for corneal endothelium without addition of Y-27632 was used for the ROCK inhibitor(−) group. At 72 hr from the start of the culture, the culture medium was exchanged and, after 72 hr, both the ROCK inhibitor(+) group and ROCK inhibitor(−) group were cultured in a normal medium for corneal endothelium free of Y-27632. On every passage, photographs of the cells were taken with a phase contrast microscope, cell density was measured, and the influence of Y-27632 on the density of the cultured monkey corneal endothelial cells was studied.

Figure 16:
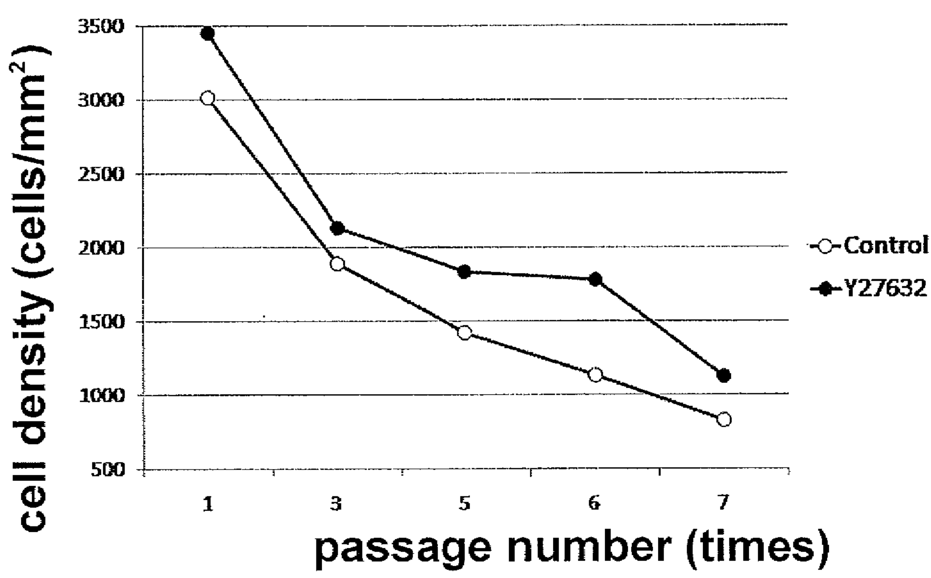
FIG. 16 is a graph showing an influence of Y-27632 on the density of cultured monkey corneal endothelial cells.

The passage was repeated 7 times, and the ROCK inhibitor(+) group showed higher cell density (FIG. 16) throughout the period of the passage culture as compared to the ROCK inhibitor(−) group. Therefrom it is considered that use of Y-27632 enables culture of corneal endothelial cells having high density, which will also be useful in the future for regenerative medicine such as transplantation of culture corneal endothelium sheet.

Example 11

Study of Influence of Fasudil on Culture of Monkey Corneal Endothelial Cell

Figure 17:
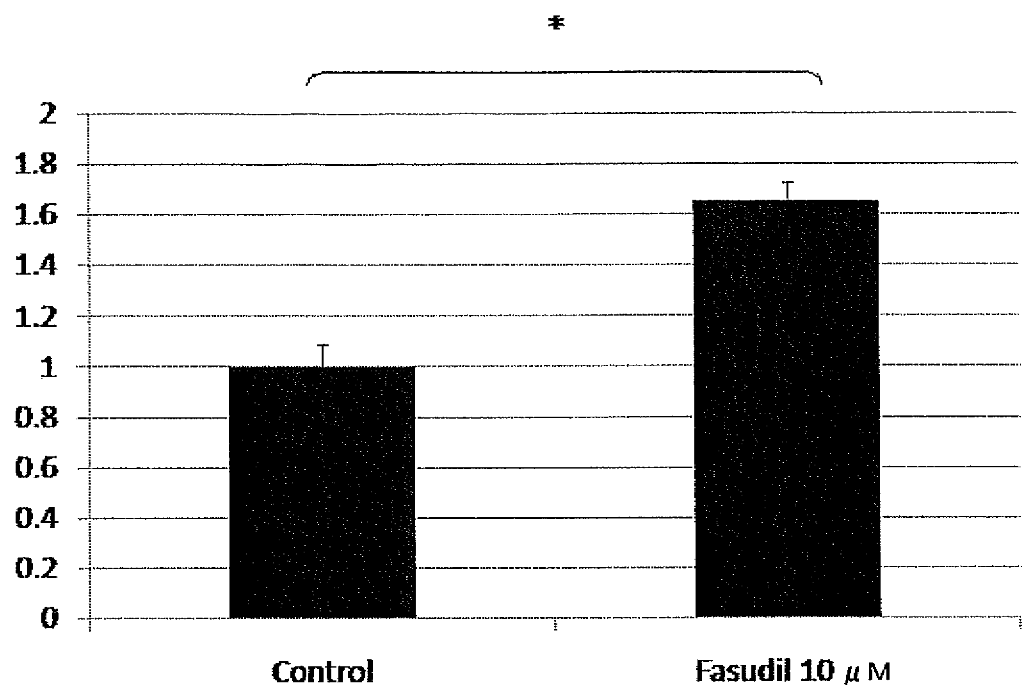
FIG. 17 is a graph showing adhesion of cultured monkey corneal endothelial cells after 24 hr from the passage culture, wherein the vertical axis shows the value of the fasudil group relative to the degree of luminescence of the control group after 24 hr from the start of the passage culture.

From the corneal tissue isolated from Macaca fascicularis euthanized, Descemet's membrane with corneal endothelial cells attached thereto was separated. The Descemet's membrane was incubated together with Dispase II (1.2 U/ml, Roche Applied Science) under the conditions of 37° C., 5% $CO_2$ for 45 min, and the corneal endothelial cells were mechanically separated by a pipetting operation. The separated corneal endothelial cells were centrifuged and passage-cultured in a medium for corneal endothelium. As the medium for corneal endothelium, the same cell culture medium as in Example 1 was used. The cultured monkey corneal endothelial cells collected during the passage culture by a 0.05% trypsin treatment were separated and centrifuged, and stirred to the same concentration in a medium for corneal endothelium added with fasudil (10 μM, SIGMA-ALDRICH) in the fasudil group and in a medium for corneal endothelium without addition of fasudil in the control group, and the cells were seeded on a 96 well plate at a density of about 2000 cells per well. At 24 hr from the start of the culture, the adhered cells were counted using CellTiter-Glo (registered trade mark) Luminescent Cell Viability Assay (Promega) (FIG. 17). An effect of promoted cell adhesion of the corneal endothelial cells was also found using fasudil, a ROCK inhibitor.

Formulation Example 5

Intracameral Injection Containing Rho Kinase Inhibitor

The following intracameral injection is prepared according to a conventional method.

| | |
|---|---|
| fasudil | 10 mg |
| sodium dihydrogen phosphate | 0.1 g |
| sodium chloride | 0.9 g |
| sodium hydroxide | e.q. |
| sterilization purified water | e.q. |
| total amount | 100 mL (pH 7) |

Formulation Example 6

Rho Kinase Inhibitor-Containing Culture Medium for Preparation of Corneal Endothelium Sheet The following culture medium is prepared according to a conventional method.

| | |
|---|---|
| fasudil | 0.5 mg |
| FBS | 10 mL |
| penicillin-streptomycin solution | 1 mL |
| FGF basic | 200 ng |
| DMEM | e.q. |
| total amount | 100 mL |

FBS manufactured by Invitrogen, penicillin-streptomycin solution manufactured by Nacalai Tesque (containing penicillin 5000 u/mL and streptomycin 5000 μg/mL), FGF basic manufactured by Invitrogen, and DMEM manufactured by Invitrogen are used.

This application is based on patent application Nos. 2007-223141 (filing date: Aug. 29, 2007) and 2008-016088 (filing date: Jan. 28, 2008) filed in Japan, the contents of which are incorporated in full herein by this reference.

The invention claimed is:

1. A method for treatment of a corneal endothelial dysfunction caused by increased intraocular pressure, comprising (i) identifying a subject currently suffering from the corneal endothelial dysfunction and (ii) administering an effective amount of a Rho kinase inhibitor to an eye of the subject to treat the corneal endothelial dysfunction in the eye of the subject.

2. The method according to claim 1, wherein the Rho kinase inhibitor is at least one selected from the group consisting of (+)-trans-4-(1-aminoethyl)-1-(4-pyridylcarbamoyl)cyclohexane, 1-(5-isoquinolinesulfonyl)homopiperazine, and pharmacologically acceptable salts thereof.

3. The method according to claim 1, wherein the eye is a human eye.

4. The method according to claim 1, comprising administering an effective amount of a Rho kinase inhibitor in the form of an intracameral injection or intraocular perfusion fluid.

5. The method according to claim 2, wherein the Rho kinase inhibitor is (+)-trans-4-(1-aminoethyl)-1-(4-pyridylcarbamoyl)cyclohexane or a pharmacologically acceptable salt thereof.

6. The method according to claim 5, comprising administering an effective amount of a Rho kinase inhibitor in the form of an intracameral injection or intraocular perfusion fluid.

7. The method according to claim 5, wherein the eye is a human eye.

8. The method according to claim 7, comprising administering an effective amount of a Rho kinase inhibitor in the form of an intracameral injection or intraocular perfusion fluid.

9. The method according to claim 2, wherein the Rho kinase inhibitor is 1-(5-isoquinolinesulfonyl)homopiperazine or a pharmacologically acceptable salt thereof.

10. The method according to claim 9, comprising administering an effective amount of a Rho kinase inhibitor in the form of an intracameral injection or intraocular perfusion fluid.

11. The method according to claim 9, wherein the eye is a human eye.

12. The method according to claim 11, comprising administering an effective amount of a Rho kinase inhibitor in the form of an intracameral injection or intraocular perfusion fluid.

13. The method according to claim 1, wherein the corneal endothelial dysfunction caused by increased intraocular pressure comprises glaucomatous attack.

14. The method according to claim 4, wherein the corneal endothelial dysfunction caused by increased intraocular pressure comprises glaucomatous attack.

15. The method according to claim 13, wherein the eye is a human eye.

16. The method according to claim 14, wherein the eye is a human eye.

* * * * *